US007369641B2

(12) United States Patent
Tsubaki et al.

(10) Patent No.: US 7,369,641 B2
(45) Date of Patent: May 6, 2008

(54) PHOTOGRAPHING APPARATUS AND THREE-DIMENSIONAL IMAGE GENERATING APPARATUS

(75) Inventors: Hidetoshi Tsubaki, Utsunomiya (JP); Toshiyuki Sudo, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 11/342,049

(22) Filed: Jan. 27, 2006

(65) Prior Publication Data
US 2006/0170674 A1 Aug. 3, 2006

(30) Foreign Application Priority Data
Feb. 1, 2005 (JP) ............... 2005-024807

(51) Int. Cl.
G21K 4/00 (2006.01)
G01N 23/04 (2006.01)
(52) U.S. Cl. .......................................... 378/41; 378/62
(58) Field of Classification Search .................. 378/4, 378/9, 19, 41, 42, 92, 62, 196; 345/419
See application file for complete search history.

(56) References Cited

U.S. PATENT DOCUMENTS

| 6,256,372 | B1 * | 7/2001 | Aufrichtig et al. ............. 378/41 |
| 6,608,884 | B1 * | 8/2003 | Mazess et al. ................ 378/98 |
| 6,764,217 | B2 * | 7/2004 | Yasuda et al. ............... 378/205 |
| 6,853,357 | B2 * | 2/2005 | Inoue et al. ...................... 345/9 |
| 6,862,364 | B1 * | 3/2005 | Berestov ...................... 382/132 |
| 6,873,866 | B2 * | 3/2005 | Briandet et al. ............. 600/407 |
| 7,035,371 | B2 * | 4/2006 | Boese et al. .................. 378/41 |
| 7,209,538 | B2 * | 4/2007 | Sukovic et al. ............... 378/42 |

FOREIGN PATENT DOCUMENTS

| JP | 10-232665 | 9/1998 |
| JP | 2000-287958 | 10/2000 |

OTHER PUBLICATIONS

Bandai, Natsuko "New Breast X-ray Photographing Method Using Three Dimensional Display", Journal of the Chubu Regional Branch of the Japanese Society of Radiological Technology, vol. 3, No. 1, pp. 178-179, (2001).
Natsuko Bandai, "New Breast X-ray Photographing Method Using Three Dimensional Display", Central District Sectional Meeting, Japan Radioactive Ray Technical Society, Central District Sectional Meeting Journal, vol. 3, No. 1, 2001. [in Japanese].

* cited by examiner

Primary Examiner—Irakli Kiknadze
(74) Attorney, Agent, or Firm—Morgan & Finnegan LLP

(57) ABSTRACT

This specification discloses a three-dimensional image pickup and display apparatus having a radiation source for applying a radioactive ray to an object, a photographing unit for photographing the transmission image of the object, and a control unit for setting three-dimensional display parameters for observing a three-dimensional image which conforms to a three-dimensional display output device. The control unit changes the position of the radiation source in conformity with the three-dimensional display parameters.

10 Claims, 13 Drawing Sheets

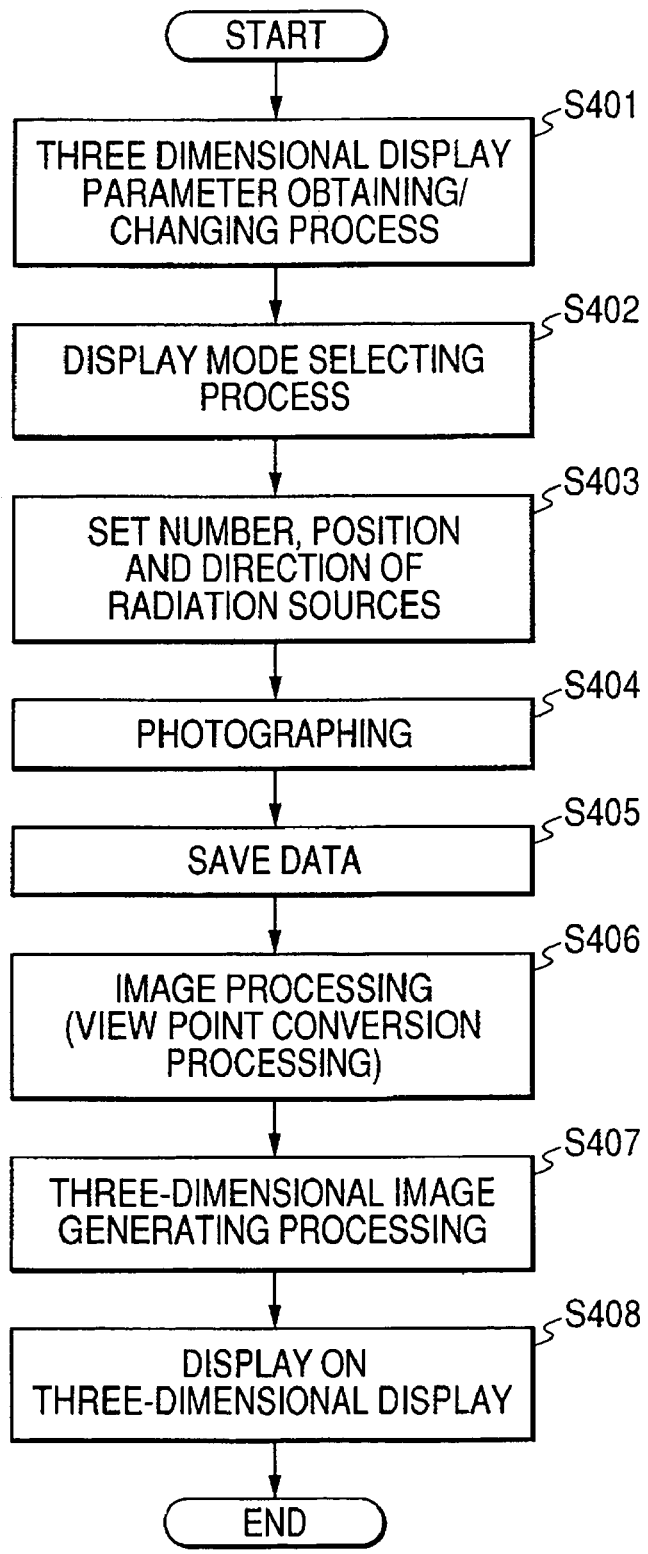

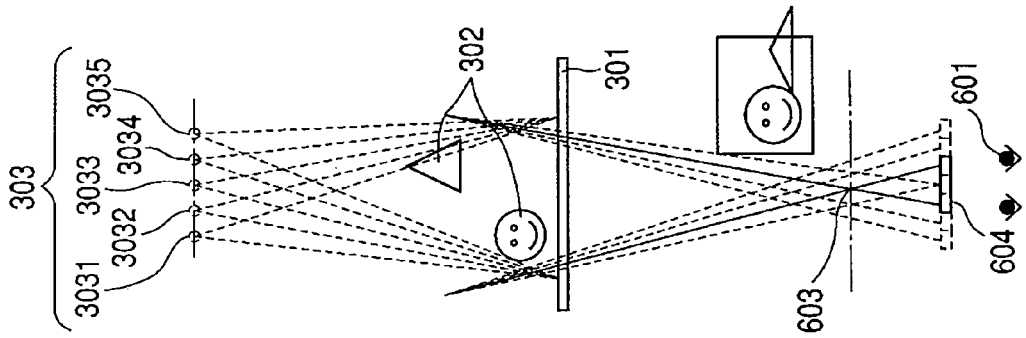
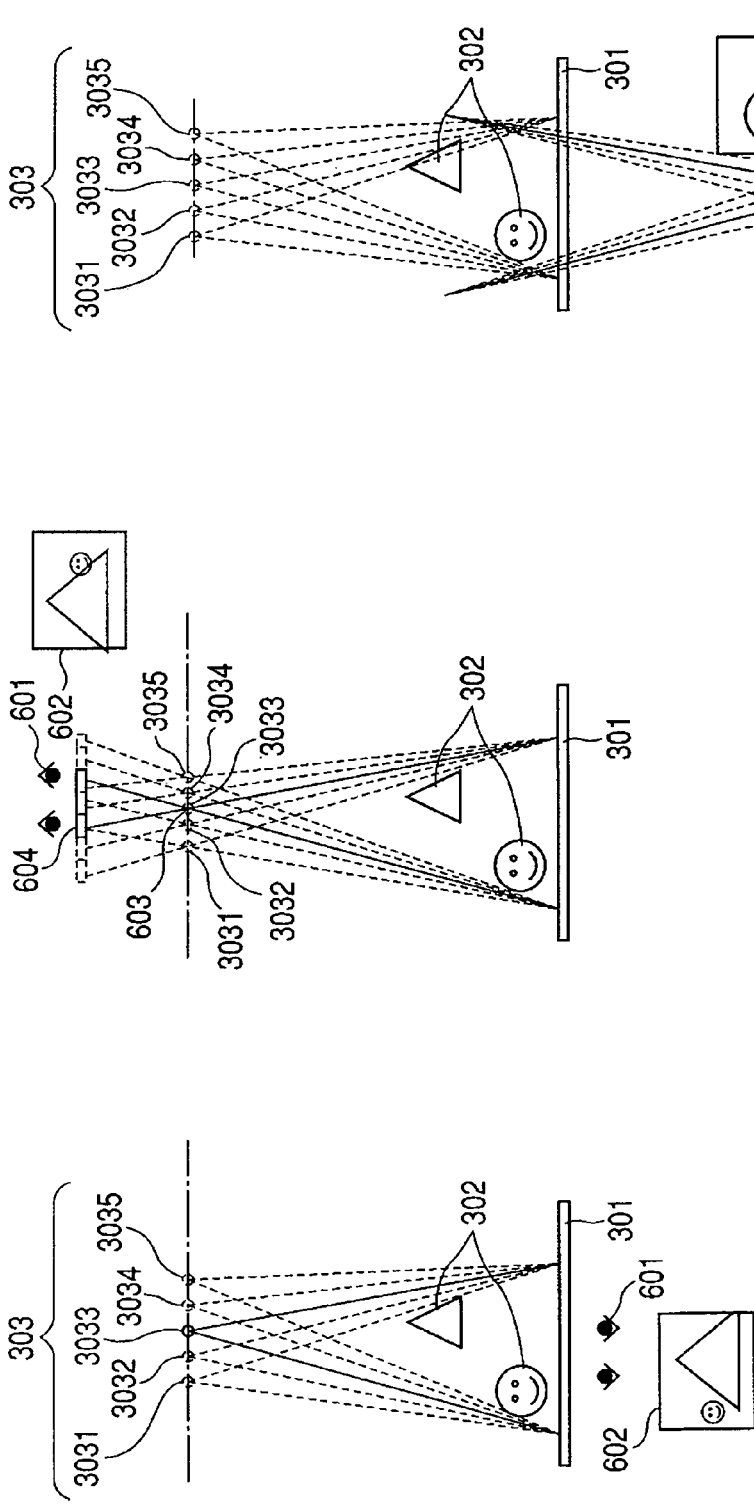

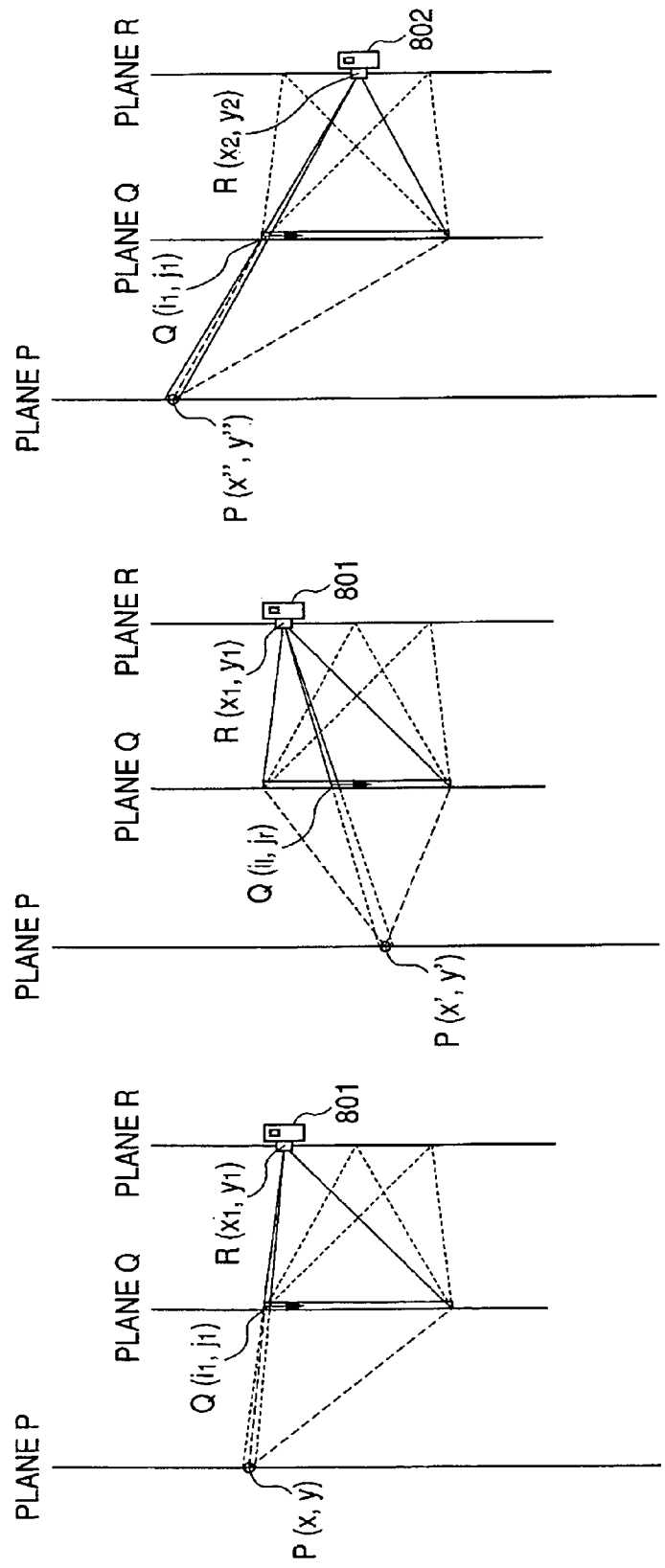

PHOTOGRAPHING APPARATUS AND THREE-DIMENSIONAL IMAGE GENERATING APPARATUS

BACKGROUND OF THE INVENTION

1. Field of the Invention

This invention relates to a photographing apparatus for photographing contents for effecting the three-dimensional display of a transmission projection image (transmission image), and further to a three-dimensional image generating apparatus for generating the three-dimensional image of the transmission image.

2. Description of the Related Art

X-ray image (transmission image) photographing is generally carried out in health screening, group medical examination, etc. in medical treatment organizations. In recent years, there has been proposed a technique of not simply photographing a transmission image, but photographing an object to be observed from the entire circumference thereof, reconstructing a plurality of photographed transmission images to thereby obtain three-dimensional voxel data, and displaying a tomographic image in any slice plane by the use of an image rendering technique.

Now, as regards the former transmission image, a transmission image having directly photographed an object to be observed can be used for medical diagnosis or the like and therefore, an image of high spatial resolution can be obtained. On the other hand, because of being a transmission image, all kinds of information of a region of the object to be observed through which a radioactive ray has been transmitted are superimposed upon one another. Therefore, from the transmission image, it is difficult to accurately grasp the distribution of a particular region (sick region) on a three-dimensional space.

Also, by displaying a tomographic image in any slice surface by the use of the latter transmission image, it is possible to easily grasp the position of the particular region on the three-dimensional space. However, there is the problem that artifact (noise) gets mixed during the reconstruction of the transmission image, and as compared with the resolution of the photographed transmission image, the resolution of the reconstructed transmission image is reduced.

So, stereoscopic observation is being reconsidered as a technique having both of these. This stereoscopic observation is to directly observe a transmission projection image and therefore has the advantage that it can observe an image of high resolution and that it is easy to grasp the stereoscopic depth disposition of a region to be observed such as a particular region by stereoscopic vision using a parallax.

As a photographing method which can be applied to the photographing of such a stereoscopic observation image, there has been a three-dimensional type radioactive ray image pickup method described in Japanese Patent Application Laid-Open No. 2000-287958 (paragraphs (0004) to (0008), FIG. 1) (corresponding U.S. Pat. No. 6,256,372). This image pickup method using a radioactive ray source is such that the radioactive ray source is moved in a predetermined plane, and the position and radiation direction thereof are adjusted to thereby photograph a plurality of view point images (images from a plurality of different view points) used for time-sharing stereoscopic observation. Then, photographed two images are stereoscopically viewed, whereby a three-dimensional image can be observed.

However, there are individual differences in the degree of ease with which an image is directly stereoscopically viewed and therefore, it is desirable to effect stereoscopic vision by the use of a three-dimensional display device (such as a lenticular lens or a barrier parallax lens) (see "New Breast X-ray Photographing Method Using Three-Dimensional Display" by Natsuko Bandai, Central District Sectional Meeting, Japan Radioactive Ray Technical Society, Central District Sectional Meeting Journal Vol. 3, No. 1, 2001).

Description will hereinafter be made of the prior art using multi-eye three-dimensional display. FIG. 6A of the accompanying drawings shows the disposition relationship of three-dimensional image observation. The reference numeral 301 designates the light receiving surface of a transmission image photographing apparatus, the reference numeral 302 denotes an object to be photographed (object to be observed), and the reference numerals 3031 to 3035 designate radioactive ray sources or the light emitting position thereof. A view point 601 is indicative of the disposition relationship of the view point (in the positional relationship with the photographing apparatus) when a transmission image photographed by the light receiving surface 301 is displayed and observed on a display device. The reference numeral 602 denotes an image obtained when the transmission image photographed in such a disposition relationship as shown in FIG. 6A is displayed.

For example, for three-dimensional image display on a three-dimensional display capable of displaying only a horizontal parallax, radioactive ray sources are moved horizontally relative to an image pickup surface, and a three-dimensional image is displayed by the use of a plurality of images having photographed the transmission image at a plurality of radioactive ray source positions. In this prior art, the object to be photographed 302 is disposed between the radioactive ray source 3031 and the light receiving surface 301, and the radioactive ray source is caused to emit light, whereby the transmission image is photographed on the light receiving surface 301. Then, as shown in FIG. 6A, the transmission image obtained in such a disposition relationship that it is looked at from the opposite side of the radioactive ray source 3031, etc. is observed.

However, when a transmission projection image (transmission image) is to be displayed on the three-dimensional display, if display corresponding to the simple disposition relationship of a three-dimensional image is effected, that is, a photographed two-dimensional image is simply displayed in conformity with three-dimensional display, the recognition of the size and positional relationship of a region to be observed obtained from the three-dimensional image deviates from the positional relationship of the actual object due to the distortion peculiar to the transmission image different from an image by an image pickup apparatus such as a camera.

Particularly, three-dimensional display has as its object to assist the recognition of the depth disposition of a focus position, but due to the depth feature (such as the magnitude relation) of the transmission image by the distortion which usually differs from that by a camera, it is difficult to discriminate between the front surface and rear surface of the three-dimensional image still after three-dimensional display is effected. Thus, there has been a case where the front surface and the rear surface are reversely recognized.

SUMMARY OF THE INVENTION

So, it is an object of the present invention to realize a photographing apparatus capable of photographing contents for realizing the suitable three-dimensional image display of a radioactive ray transmission image.

An image pickup apparatus as a point of view of the present invention has a radiation source for applying a radioactive ray to an object, a photographing unit for photographing the transmission image of the object, and a control unit for setting three-dimensional display parameters for observing a three-dimensional image conforming to a three-dimensional display output device, and is characterized in that the control unit changes the position of the radiation source in conformity with the three-dimensional display parameters.

Also, an image generating apparatus as another point of view of the present invention is characterized by a photographing unit for photographing the transmission image of an object to which a radioactive ray is applied by a radiation source, a control unit for setting three-dimensional display parameters for observing a three-dimensional image conforming to a three-dimensional display output device, and an image processing unit for generating an image different from the transmission image photographed on the basis of the three-dimensional display parameters by the photographing unit.

BRIEF DESCRIPTION OF THE DRAWINGS

FIG. 3 is a flow chart of the three-dimensional image pickup and display apparatus according to Embodiment 1 of the present invention.

FIGS. 6A and 6B illustrate a photographing method for and the display form of a transmission image according to the prior art.

FIG. 6C shows the display form (display mode) of a transmission image according to Embodiment 1 of the present invention.

FIGS. 12A, 12B and 12C are typical views showing the image conversion processing according to Embodiment 1 of the present invention.

DESCRIPTION OF THE PREFERRED EMBODIMENTS

An embodiment of the present invention will hereinafter be described.

Figure 1:
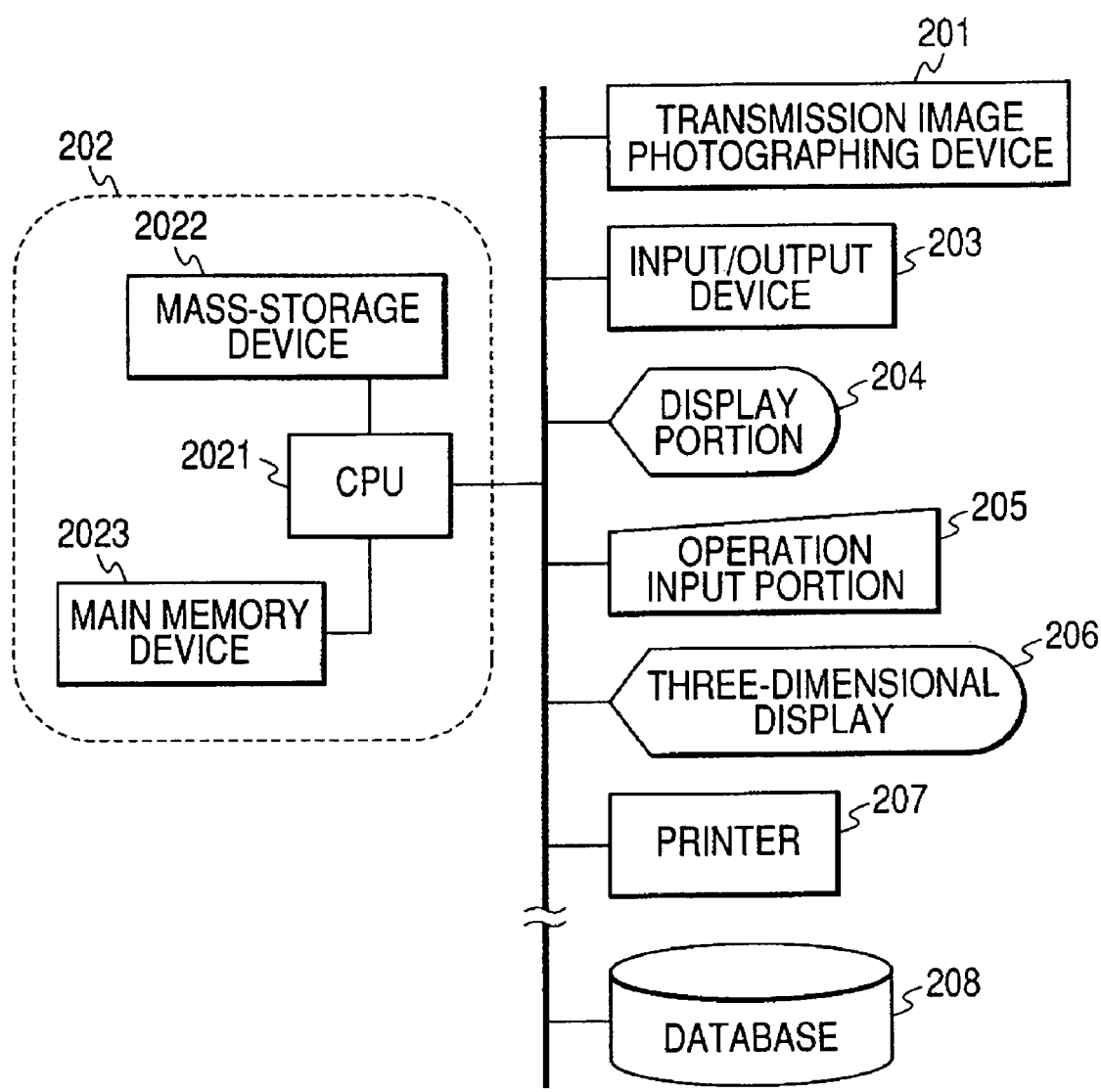
FIG. 1 is a schematic view of a three-dimensional image pickup and display apparatus according to Embodiment 1 of the present invention.

Description will hereinafter be made of a three-dimensional (3D) image pickup and display apparatus according to Embodiment 1 of the present invention. FIG. 1 is a block diagram of the three-dimensional image pickup and display apparatus according to the present embodiment, and FIG. 2 is a block diagram of a transmission image photographing apparatus constituting a portion of the three-dimensional image pickup and display apparatus according to Embodiment 1.

Figure 2:
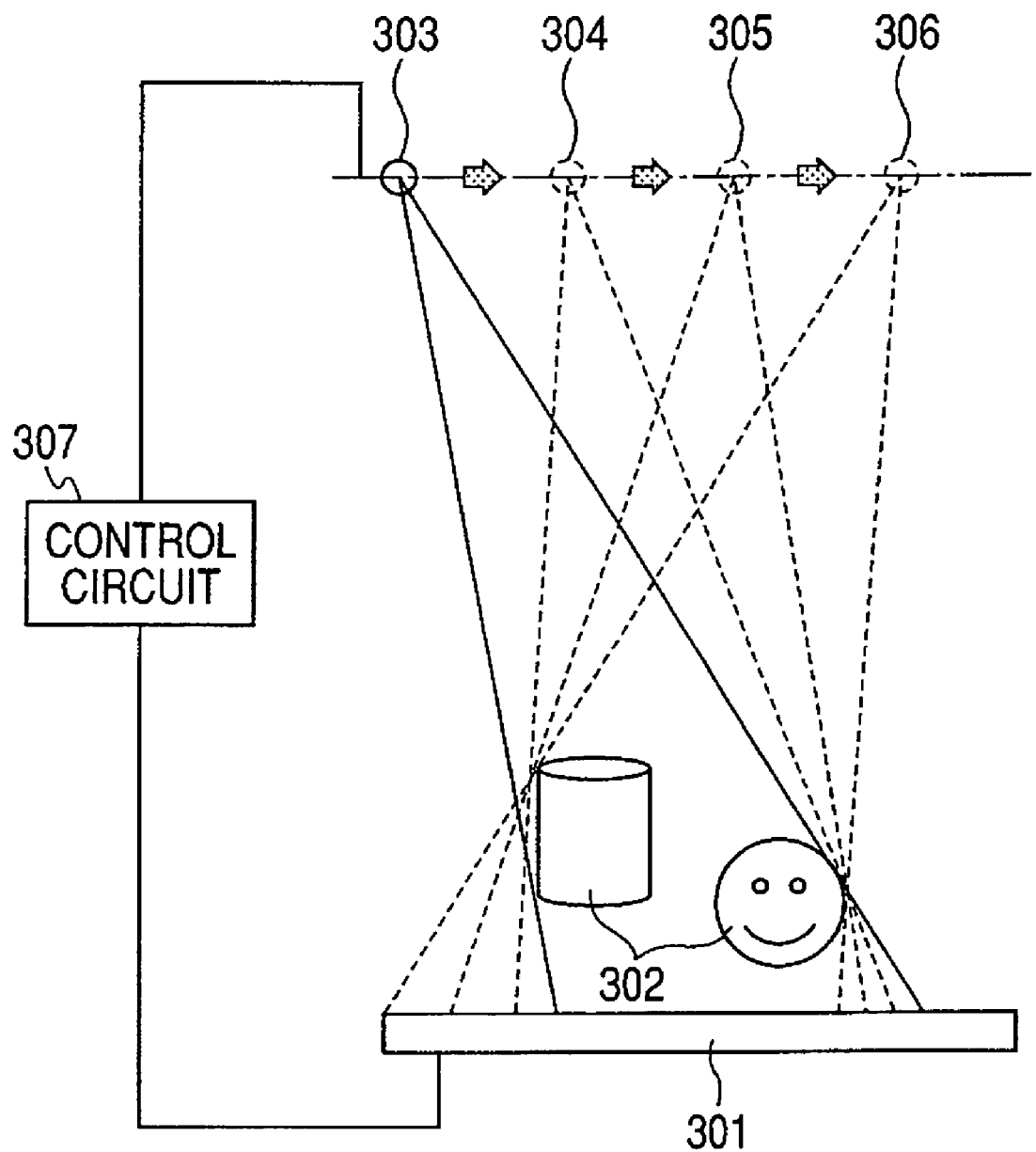
FIG. 2 is a construction block diagram showing a radioactive ray transmission image photographing apparatus according to Embodiment 1 of the present invention.

The reference numeral 201 designates the transmission image photographing device, which is comprised of a light receiving element (photoelectric conversion element) 301 and movable radioactive ray sources 303 to 306, as shown in FIG. 2. These radioactive ray sources (which, even if simply referred to as the "radiation sources", mean radioactive ray sources) may be constituted by a radioactive ray source array disposed on a flat surface or a quadratic surface.

Also, as will be described later, provision is made of a control circuit 307 for controlling the positional relationship between the radioactive ray sources 303 to 306 and the light receiving element 301. The reference numeral 302 designates an object to be photographed (an object of observation), and radioactive rays emitted from the radioactive ray sources 301 to 306 are applied to the object to be photographed 302. The radioactive rays transmitted through this object to be photographed 302 are received on the light receiving surface of the light receiving element 301 (and an electric current or the like corresponding to the intensity of the radioactive rays is generated), whereby the intensity of the radioactive rays is detected.

The reference numeral 202 denotes a three-dimensional image processing device. This device converts inputted transmission image data corresponding to a plurality of view points into image data suited for being displayed as a three-dimensional image, and outputs the converted image data (as an image signal) to a three-dimensional (3D) image display 206. Also, the three-dimensional image processing device 202 effects the control of the transmission image photographing apparatus 201 through a control circuit 307 and also, effects the calculation of the positions of the individual radioactive ray sources suitable for three-dimensional display parameters which will be described later. This three-dimensional image processing device 202 is constituted, for example, by a universal engineering work station and a personal computer. The three-dimensional image processing device may also be constituted by the use of other calculating device.

The reference numeral 203 designates an input/output device which reads and writes data recorded on a fixed recording medium such as a Floppy (registered trademark) disk, MO (registered trademark), ZIP (registered trademark), CD-ROM, CF card (registered trademark) or Smart Media (registered trademark). The input/output device 203 functions as an input/output portion with respect to an external device or the like, and outputs photographed transmission image data and synthesized three-dimensional image data, and inputs formerly photographed transmission image data. Also, in a case where among three-dimensional display parameters, the number of view points which is information inherent to a three-dimensional display output device and information regarding a supposed observation distance are given as file data, they are inputted from this input/output device 203.

Also, the input/output device 203 may be constituted by the network port of an ethernet or the like connected to a network, an antenna, a receiver and a transmitter for effecting the reception of data distribution by broadcasting, and radio communication. By so constructing, it is also possible to obtain transmission images corresponding to a plurality of view points and three-dimensional display parameter data through various networks.

This input/output device 203 may also be constituted as a portion of a cable connected to transmit an image signal to a three-dimensional display 206. By so constructing, the input/output device 203 can be a data bus capable of taking out a display parameter inherent to a three-dimensional display (three-dimensional display output device) regarding three-dimensional display from the firmware data of the three-dimensional display 206.

The reference numeral 204 denotes the display portion (display) of the three-dimensional image processing device 202. It obtains information necessary for three-dimensional image conversion and display in the fashion of a dialog, assists the obtainment of the information, and displays the processing situation, a menu, transmission images corresponding to a plurality of view points constituting a three-dimensional image which is the result of conversion, a time-sharing three-dimensional image, etc.

The reference numeral 205 designates an operation input portion constituted by a mouse or a keyboard, a joy stick, etc., and it is used to select a menu or input data while looking at a menu image displayed on the display portion 204. By constituting the display portion 204 by a touch panel, or constituting the operation input portion 205 by the use of voice recognition or a gaze input or the like, it is also possible to constitute the operation input portion without providing the keyboard, the mouse, the joy stick, etc.

The reference numeral 206 denotes a three-dimensional display. The three-dimensional display 206 is an example of a three-dimensional display output device. Here, the three-dimensional display 206 means an entire display device, and the three-dimensional display device refers to a ray deflection optical element which is the key component of the three-dimensional display device. For example, if it is one which effects the modulation of the brightness of a ray of light for each pixel by a liquid crystal display device, it is installed immediately behind the liquid crystal display device, and a lenticular sheet for deflecting the direction of a light ray emitted to a space corresponds to it. The three-dimensional display 206, after the conversion processing of the transmission image by the three-dimensional image processing device 202, displays a stereoscopically viewable image by the use of transmission image data subjected to the conversion processing. Hereinafter, the three-dimensionally viewable image displayed on the three-dimensional display 206 or the like will be simply referred to as the "three-dimensional image".

The three-dimensional display 206 is designed to be capable of dynamically converting two-dimensional display and three-dimensional display (see Japanese Patent Application Laid-Open No. H10-232665 (corresponding U.S. Pat. No. 6,023,277). That is, a single three-dimensional display 206 can be given the function of displaying a three-dimensional image (showing the three-dimensional image to an observer) and the function of displaying a two-dimensional image (showing the two-dimensional image to the observer).

In this case, it is desirable to set the image displaying method of the three-dimensional display 206 so as to be changeable over so that only the image data received as three-dimensional image data may be displayed as a three-dimensional image and the other data than the three-dimensional image (i.e., image data as the two-dimensional image) may be displayed as a two-dimensional image. Specifically, the light intercepting position of a mask member the three-dimensional display has is controlled or an optical element such as a lenticular sheet the three-dimensional display has is driven to thereby effect the changeover of the three-dimensional image and the two-dimensional image.

The reference numeral 207 designates a printer for printing the three-dimensional image. This printer 207 is also an example of the three-dimensional display output device. This printer is a printer for printing the three-dimensional image converted and synthesized by the three-dimensional image processing device 202, and is not restricted to a universal printer for printing on an ordinary medium such as paper or film. It may be, for example, a printer directed to the printing of a three-dimensional image. Specifically, it may be a printer capable of directly printing on a deflection optical element or a polarization optical element for displaying a three-dimensional image, such as a lenticular sheet or an integral sheet, or a micropole made into a sheet shape. It may also be a holographic stereogram printer or the like for converting an image corresponding to a plurality of view points into hologram information and printing it as three-dimensional information.

These media for printing the three-dimensional image thereon usually have three-dimensional display parameters different from that of the three-dimensional display 206 about the number of view points and the supposed observation distance. Therefore, three-dimensional image print data is converted and synthesized by three-dimensional display parameters different from that during the display.

The reference numeral 208 designates a data base on a network. It preserves therein the data file of the transmission images corresponding to a plurality of view points and three-dimensional display parameters data corresponding to each three-dimensional display while relating them with a key word.

The construction of the three-dimensional image processing device 202 will now be described. The reference numeral 2021 denotes a central processing circuit (CPU) which governs the control of the entire device. The reference numeral 2022 designates a mass storage device which is a memory device which preserves therein the transmission images corresponding to a plurality of view points read in by the input/output device 205 or the like, and preserves therein three-dimensional image data converted (generated) from a plurality of projection images into an image for three-dimensional display. This mass storage device 2022 is constituted by a hard disk or the like, and likewise has the role as a data base regarding the three-dimensional display parameters.

The reference numeral 2023 denotes a main memory device constituted by a RAM or the like. This main memory device 2023 evolves a program, the inputted transmission image data corresponding to a plurality of view points, and the three-dimensional display parameters. Also, the main memory device 2023 primarily stores therein the three-dimensional image data after converted, before such data is displayed, or before such data is stored in the mass storage device 2022, or before such data is outputted from the input/output portion 203, that is, the main memory device 2023 primarily stores therein the three-dimensional image data after converted, before such data is displayed, stored or outputted.

In the present embodiment, the transmission image photographing device 201 and the three-dimensional image processing device 202 are constructed as a single three-dimensional image pickup and display apparatus. However, it is also possible to control the three-dimensional image processing device 202 in conformity with a three-dimensional display parameters inputted or set by the use of a control circuit 307 provided in the transmission image photographing device 201. That is, at least one of the control circuit 307 of the transmission image photographing device 201 and the central processing circuit 2021 of the three-dimensional image processing device 202 operates as a control unit for setting the three-dimensional display parameters.

The three-dimensional display parameters in the present embodiment will now be described. Each of the three-dimensional display parameters is a parameter calculated or determined in conformity with the characteristic of the three-dimensional display.

1) Number of View Points: This is the number of view points the three-dimensional display 206 has, and for example, in the case of the direct display of a stationary image, it corresponds to the number of transmission images corresponding to a plurality of view points at a radiation source position for photographing to display a three-dimensional image.

2) Display Size: This is the size of a three-dimensional image on the display surface of the three-dimensional display 206. In other words, it is an index indicative of a display range or a view field range in a direction horizontal to the display surface of the displayed three-dimensional image.

3) Supposed Observation Distance: This is an observation distance suitable for the observation of the three-dimensional image supposed in individual three-dimensional displays. This supposed observation distance is a design parameter, and usually becomes different among three-dimensional displays having different characteristics. A view region or the like is optimized so that the observation state of the three-dimensional image at the supposed observation distance may be good. That is, a region in which the three-dimensional image can be observed in the observation plane (observation region) is optimized in position, shape, area, etc.

4) Number of Image Steps: This is a parameter regarding the number of steps representative of the relation between parallax images incident on the right and left observing eyes when the three-dimensional image displayed on the three-dimensional display 206 is observed at the supposed observation distance.

In a multi-eye three-dimensional display for displaying an image having a parallax corresponding to three or more view points, the base length of a three-dimensional image at the supposed observation distance is shorter in some cases than the distance between the human eyes. In such a three-dimensional display, there is a case where images displayed as adjacent parallax images are not incident on the right and left observing eyes, but the images at desultory view points are incident on the right and left eyes. That is, there is a case where among the images corresponding to a plurality of view points displayed by the three-dimensional display, two images of which the view points are not adjacent to each other are incident on the observer's right and left eyes. Here, the base length is the distance between the central positions of view regions in which two adjacent parallax images are displayed at the observation position (observation plane).

For example, in a case where the images at adjacent view point positions are given view point numbers 1, 2, 3, 4, . . . , assuming that the image incident on the left eye is image 1, the images are incident on the observing eye at a certain step number in such a manner that the image incident on the right eye is image 3 (i.e., step number 2) or image 4 (step number 3).

Figure 5A:
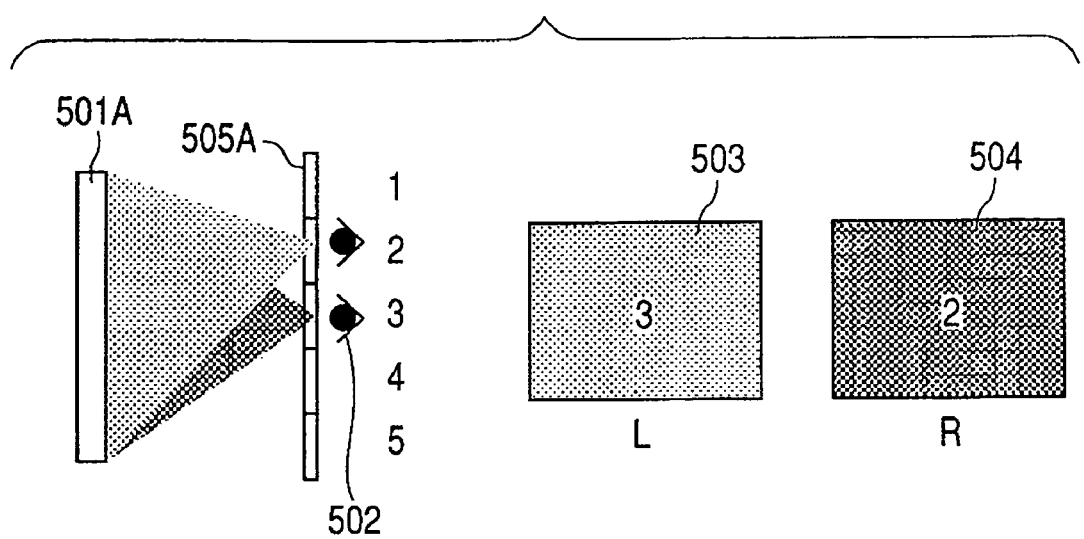
FIGS. 5A and 5B are illustrations of the number of the observing eye incident image interval steps of the three-dimensional display parameters according to Embodiment 1 of the present invention.
Figure 5B:
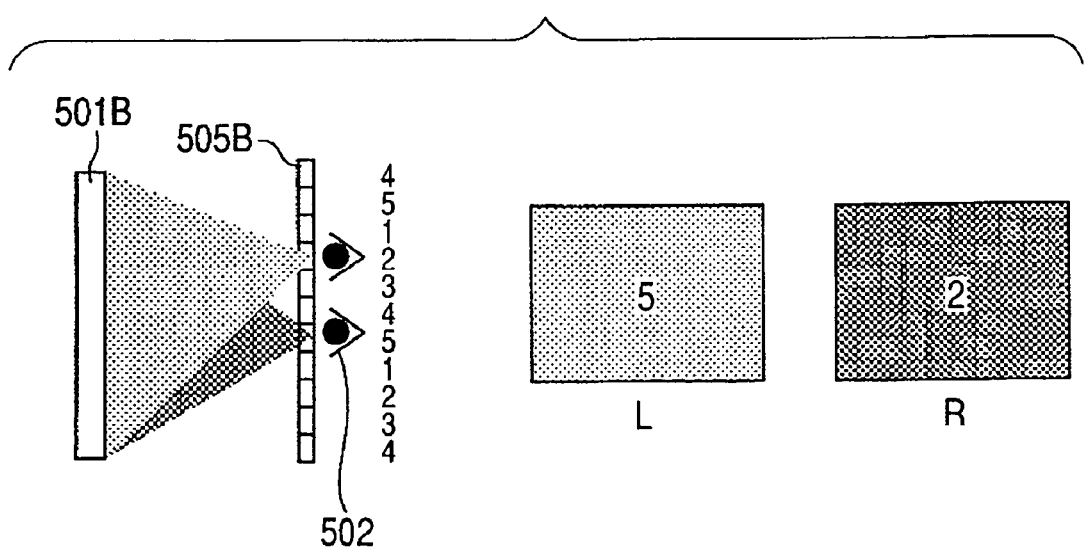

FIGS. 5A and 5B show the manner of difference between the step numbers when the three-dimensional image is observed at the same supposed observation distance by the use of two three-dimensional displays having different characteristics. Here, the image step number is a numerical value representative of what number the view point of the parallax image incident on the right eye is as counted from the view point of the parallax image incident on the left eye when among a plurality of parallax images obtained by observing the object to be photographed from a plurality of different view points, the plurality of parallax images displayed by the three-dimensional display are arranged in the order in which the view points are arranged. That is, in a case where the parallax images from two adjacent view points are observed by the right and left eyes, the observing eye incident image interval step number is 1. In other words, the image step number is a numerical value representative of how many times as great as the base length the interval between the right and left eyes is in the observation region (or the observation plane).

Usually, the three-dimensional display can display two or more images photographed at equal base length intervals with respect to a horizontal direction, and depending on the situation, a vertical direction in addition to the horizontal direction, in parallel by the number of view points inherent to the three-dimensional display, to thereby display a three-dimensional image observable by multiple persons.

In FIGS. 5A and 5B, the reference characters 501A and 501B designate the display surfaces of the three-dimensional display, the reference numeral 502 denotes the observer's view point, the reference numeral 503 designates the view point number of a parallax image incident on and observed by the left eye, and the reference numeral 504 denotes the view point number of a parallax image incident on and observed by the right eye. The reference characters 505A and 505B designate markers illustrating the region distributions of the displayed images of the three-dimensional images at the observation distance, and the markers are actually not visually perceived. As shown in FIG. 5A, changeover occurs so that the parallax image of view point 2 may be seen in the region wherein the marker 505 is present, and when the view point leftwards in the horizontal direction relative to the display surface 501A, the parallax image of view point 3 may be seen.

In the displays 501A and 501B of FIGS. 5A and 5B, respectively, however, the same supposed observation distance is set, but the two differ in images incident on the right and left eyes from each other. That is, in the three-dimensional display of FIG. 5A, adjacent view point images constituting the three-dimensional image at the same supposed observation distance are incident on the right and left eyes. Here, the adjacent view point images are images seen from two adjacent view points, among the images displayed by the three-dimensional display 206 and obtained by looking at the object to be photographed from a plurality of different view points.

In contrast, in the three-dimensional display shown in FIG. 5B, an image likewise having five view points, i.e., the view point 1, the view point 2, . . . , the view point 5 is repetitively displayed in space and therefore, the separation width is narrow than that of the display 501A shown in FIG. 5A. Thus, for example, the image incident on the left eye is the image of the view point 2 and the image incident on the right eye is the image of the view point 5, and the view point images of the step number 3 skipped by two view points are incident on the right and left eyes. In other words, the three-dimensional display displays the image of the object to be photographed as it is seen from the five view points, i.e., the different view points 1 to 5 (desirably three or more view points), and design is made such that among the images from the five view points, two images of which the view points are not adjacent to each other are directed to the right and left eyes.

As described above, the relation between the images incident on the two observing eyes at the same observation distance is represented by the parameter of the step number.

Specifically, in a case where a three-dimensional image constituted by images photographed between two three-dimensional displays by the same base length unit and corresponding to a plurality of view points is displayed, the relation between the base lengths of the multi-view point images incident on the two eyes differs and therefore, for example, as compared with FIG. 5A, the flying amount and sinking amount of the three-dimensional image in FIG. 5B become three times as great, thus more giving a three-dimensional feeling.

Therefore, there arises the problem that the same three-dimensional feeling is obtained even if a three-dimensional image constituted by the same row of images is observed at the same geometrical disposition, but this problem can be avoided by considering the image step number to be three-dimensional display parameters. The image step number is also a design parameter, and differs from one three-dimensional display to another differing in characteristic.

Also, if the three-dimensional display is constructed on the basis of a three-dimensional display system such as a lenticular lens or an integral photograph, the image step number is changed in accordance with the observation distance to the observing eye with the display surface as the reference or a spatial position. Accordingly, in order to cope with a great fluctuation in the observer's view point position, the image step number is given as a function or a table having the coordinate parameter of the observation view point as an argument. Here, the coordinate parameter of the observation view point is a value regarding the relative position of the observing eye to the three-dimensional display.

As the result, it is necessary to use this coordinate parameter of the observation view point as a secondary parameter for finding the image step number. As regards the coordinate parameter of the observation view point, the coordinates are successively found by the use of a head position detecting sensor comprising a combination of an azimuth sensor and a magnetic sensor, or by the use of a vision sensor. On the basis of the found coordinates, whether a change has occurred to the image step number is checked up at real time to thereby calculate the image step number.

5) Limit Range of Display Three-Dimensionality: This is the maximum and minimum range of a parallax amount which can be presented on the display surface. That is, it is a maximum amount of sinking and a maximum amount of jumping-out from the display surface capable of displaying as a three-dimensional image. Originally, the range of such a display parallax amount should be restricted by the image-fusible range of the human eye physiologically determined. However, the ordinary three-dimensional display is not complete, but is restricted to a range narrower than the image fusion limit of man by such factors as the conflict between the parallax of two eyes and adjustment, and the cross talk between adjacent images. This range depends on the design parameter of the three-dimensional display and the emission process of a ray of light, and differs from one three-dimensional display to another. Also, this limit range of display three-dimensionality is a parameter obtained from the experimental data and evaluation result of the allowance experiment of a three-dimensional image.

Here, the physiologically determined image-fusible range is, firstly, the closest distance at which a parallax amount corresponding to maximum jumping-out enables man to recognize an object as one. It is a parallax amount (amount of jumping-out) corresponding to a three-dimensional image existing at about 15 cm before the eyes, and next, is the range of a parallax amount (amount of sinking) corresponding to the fact that a parallax amount corresponding to maximum sinking corresponds to a three-dimensional image existing at infinity, i.e., a parallax amount corresponding to the distance between one's eyes (see Noriaki Kumada, "About the Design of a 3D Image", Broadcasting Technique, November 1992, pp. 119-125). More simply expressing, the image-fusible range is representative of a maximum amount of jumping-out, amount of sinking or parallax at which man can fuse two parallax images into one and observe them as a three-dimensional image.

Thus, the displayed parallax range is restricted by smaller one of a parallax range limited by the image fusion limit and a parallax range limited by the limit range of display three-dimensionality. The limit range of display three-dimensionality is indicated by the range of the parallax which can be displayed on the display surface or an image data scale. Or it can be represented by the interval of the image pickup view point between adjacent view point images by the use of the value of an image step number taking the photographing parameter of the photographing apparatus into consideration, and can also be converted.

The zoom ratio and three-dimensionality which will hereinafter be described are arbitrary parameters adjusted in conformity with a user observing the three-dimensional display.

6) Zoom Ratio: This is representative of the enlargement ratio of display when the user selects a region and partly enlarges a portion of a three-dimensional image. The user may select a region as a zoom region in a predetermined three-dimensional image photographed by a user interface, and display it on an enlarged scale.

7) Three-Dimensionality: This is a parameter indicative of the degree of adjustment of the three-dimensional feeling, and by adjusting this three-dimensionality, it is possible to strengthen or weaken the three-dimensional feeling. To strengthen the three-dimensional feeling between parallax images from a reference state, photographing at a base line length still greater than in the reference state is effected. More particularly describing, it is necessary to widen the distance between two view points when two parallax images made incident on the right and left eyes are photographed, that is, between image pickup apparatuses when two parallax images are photographed.

Simply, the distance between two adjacent view points during photographing (photographing base line length) may be widened. Conversely, to weaken the three-dimensional feeling, the converse can be done, and the distance between two view points when the two parallax images made incident on the right and left eyes are photographed (between the image pickup apparatuses when the two parallax images are photographed) can be narrowed. Of course, the photographing base line length may simply be narrowed. Or when the three-dimensional display is to display a parallax change only in a horizontal direction, it is also possible to make such design that horizontal shift is effected between parallax images constituting a three-dimensional image so as to adjust the balance between jumping-out and sinking.

This three-dimensionality parameter can be neglected when a natural three-dimensional feeling is displayed faithfully to the display scale. When the display parallax range of the displayed three-dimensional image after the adjustment exceeds the limit range of display three-dimensionality, priority is given to one of the degree of three-dimensional feeling and the limit range to thereby adjust the three-dimensionality. When priority is given to the limit range, adjustment is effected so as to scale the display parallax amount so that the limit range may be the display limit range of the three-dimensional display. Or the offset of the parallax amount is increased or decreased to thereby adjust the balance between jumping-out and sinking.

8) Presence Range of the Object to Be Photographed: This is the presence area range of the object to be photographed disposed between the radioactive ray source and the light receiving surface in a direction linking the light source surface and the light receiving surface together. A value is set and inputted as a parameter, or the occupied area by the object to be photographed is detected and set by the use of a vision sensor. In a case where a three-dimensional image having a wide display parallax range is displayed by a three-dimensional display having a very narrow display three-dimensionality limit range, this becomes a parameter necessary to display a three-dimensional image easy to see and free from an unpleasant feeling.

The operation flow in the three-dimensional image pickup and display apparatus according to the present embodiment will now be described with reference to FIG. 3.

<Process of Obtaining and Changing the Three-Dimensional Display Parameters (Step 401)>

First, at a step 401, the three-dimensional image processing device 202 obtains the three-dimensional display parameters of the three-dimensional display 206. These three-dimensional display parameters are used to determine the frequency of light emission, the light emitting position and interval, and the light emitting direction of the radioactive ray source when the transmission image is photographed to display one or a plurality of three-dimensional images.

The three-dimensional display parameters are obtained by operating the operation input portion 205 to thereby input a new value to be changed, or inputting data including the three-dimensional display parameters from the input/output device 203 while referring to a predetermined value displayed on the screen of the display portion (display) 204, or observing a three-dimensional image displayed on the three-dimensional display 206.

Also, the CPU 2021 always monitors the changeover of the three-dimensional display, the movement of the zooming observation view field, any change in a zooming parameter, the adjustment of the three-dimensionality parameter, any change in the presence range of the object to be photographed, a demand for the changing of the parameters from the user interface, etc., and carries out the process of obtaining, changing and renewing the latest three-dimensional display parameters in conformity with the changing of the parameters.

Further, in the process of obtaining and changing the three-dimensional display parameters at this step 401, the three-dimensional display parameters are inputted from the operation input portion 205 by the use of GUI displayed on the display 204 or the three-dimensional display 206, or the three-dimensional display parameters are obtained by the use of a data file inputted from the input/output device 203.

The presence range of the dynamically changing object to be photographed 302 is obtained, for example, by providing a sensor for monitoring the space between the radioactive ray sources 301 to 306 of the transmission image photographing device 201 and the light receiving surface 301. If all the three-dimensional display parameters are unobtained, the obtainment of all three-dimensional display parameters is effected, but at the second and subsequent times, the process of obtaining and changing the three-dimensional display parameters are carried out for only the item in which the changing of the three-dimensional display parameters at the step 401 has been detected.

<Display Mode Selecting Process (Step 402)>

Next, a display mode is selected from a GUI menu displayed on the display portion 204 or the three-dimensional display 206.

This display mode relates to the position of the transmission images corresponding to a plurality of view points constituting a three-dimensional image relative to the object to be photographed during the photographing thereof (the position of the image pickup surface during photographing relative to the object to be photographed) and the positional relation between the three-dimensional image and the view points when the three-dimensional image is displayed on the three-dimensional display 206. The display mode (the positional relation of an imaginary view point position when the three-dimensional image is displayed to the object to be photographed) has the following three kinds shown in FIGS. 6A, 6B and 6C, including the conventional example, and one of these three display modes is selected from GUI.

FIG. 6A shows a view point similar to a conventional radioactive ray transmission image (display mode A). An object to be photographed 302 is disposed between a radioactive ray source 303 and a light receiving element 301, and the radioactive ray source 303 is caused to emit light, and a transmission image is obtained on the light receiving element 301. In FIG. 6A, the transmission image obtained at a position whereat the light receiving element 301 is opposed to the radioactive ray source 303, i.e., in such an arrangement that the observer looks into from the opposite side of the light receiving element 301 is observed. The obtained transmission image is used to constitute a three-dimensional image.

FIG. 6B, like FIG. 6A, shows a conventional view point positional relation in which the object to be photographed 302 is disposed between the radioactive ray source 303 and the light receiving element 301, and the radioactive ray source is caused to emit light and a transmission image is obtained on the light receiving element (display mode B). Then, mirroring process is effected on the obtained transmission image. As the result, from the geometrical relation between the radiation source position and the light receiving element 301, the mirroring transmission image becomes similar to an image obtained by a pinhole camera provided by a light receiving surface being installed on a side opposite to the actual light receiving surface with the radiation source position as a pinhole position. That is, there is obtained an image equivalent to a three-dimensional image constituted by an image having its view point shifted to the radiation source side, and obtained by the object to be photographed 302 being photographed by the pinhole camera.

FIG. 6C shows the characteristic relation of the view point position of the present embodiment to a three-dimensional image (display mode C). First, the radioactive ray source 303 is moved in a plane parallel to the light receiving element 301 to thereby photograph transmission images from a plurality of view points for constituting a three-dimensional image. Then, a radiation source position on the opposite side of the radiation source 303 is set, that is, a view point position on the opposite side is set, and by the use of each pixel in a corresponding imaginary light receiving surface and the relative positional relation, an imaginary transmission image is generated from the image data of a transmission image already photographed at the position of the radiation source 303. Thereby, it is possible to obtain such a transmission image that the radioactive ray source is located on the same side as the observation view point relative to the light receiving element 301.

As described above, in the display mode C, it becomes possible to change over the display to an imaginary image for which the positional relation between the observation view point position relative to the light receiving element 301 and the radioactive ray source has been changed, without changing the position of the object to be photographed, and it becomes possible to provide various view point images.

<Process of Determining the Number of Radiation Sources, Position of Radiation Sources and Application Direction of Radiation (Step 403)>

At a step 403, the process of changing the position and direction of the radiation sources is carried out. In order to generate a three-dimensional image from which a suitable three-dimensional feeling can be obtained, by the use of the three-dimensional display parameters inputted at the step 401 and the display mode displayed and selected at the step 402, the frequency of light emission, position and direction of the radioactive ray sources when transmission images corresponding to a plurality of radioactive ray source positions are photographed are determined (set). Description will hereinafter be made of a method of setting the position and direction of the radioactive ray sources taking the display modes and the three-dimensional display parameters into account.

In the display mode A (FIG. 6A), the number of the radioactive ray sources is determined by the view point number parameter of the three-dimensional display parameters. The frequency of light emission is the same as the view point number of the three-dimensional display parameters. Next, the interval between the radioactive ray sources is determined. First, only two radioactive ray sources are supposed on the supposed observation distance, and the interval between the two radioactive ray sources which becomes the reference for determining the intervals among all radioactive ray sources, that is, which constitute images incident on the right and left eyes in the imaginary observation distance is determined. When in the row of the radioactive ray sources, observation is effected at the supposed observation distance, two radioactive ray sources separate by the image step number from each other which are incident on the observing eyes correspond to these two radioactive ray sources.

Besides the interval between the radioactive ray sources, the distance between the radioactive ray sources and the light receiving element, and in some cases, the size of the light receiving surface of the light receiving element may be adjusted in accordance with the supposed observation distance and the display size. Further, instead of changing the size of the light receiving surface, the picked-up parallax image may be reduced or enlarged during the display thereof.

Figure 4A:
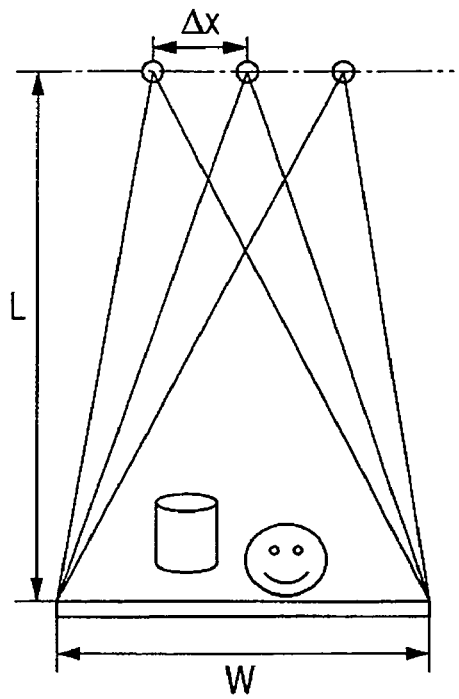
FIGS. 4A and 4B are geometrical relation illustrations of the setting of three-dimensional display parameters according to Embodiment 1 of the present invention.
Figure 4B:
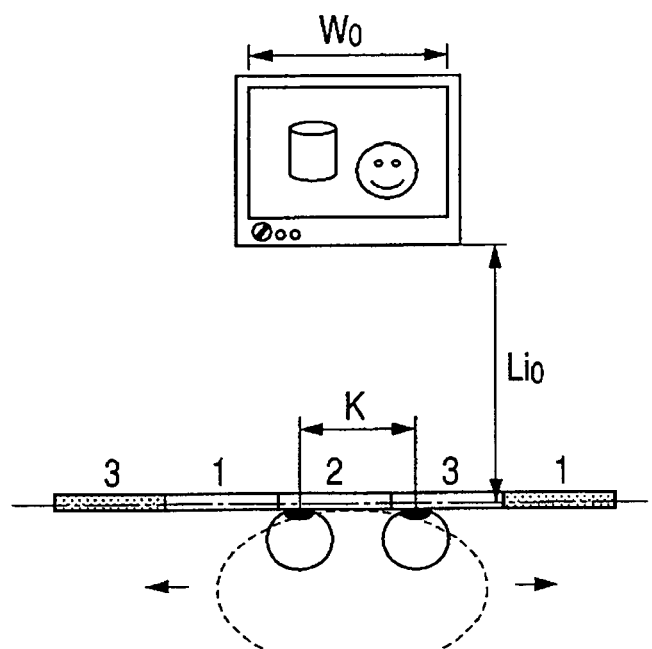

FIGS. 4A and 4B illustrate the geometrical relation of the setting of the three-dimensional display parameters. FIG. 4A shows the parameter for during photographing, and shows the relations among the radioactive ray source array, the object to be photographed and the light receiving surface. The interval between the radioactive ray sources is defined as $\Delta x$, the distance between the radioactive ray sources and the light receiving surface is defined as L, and the size of the light receiving surface is defined as W.

FIG. 4B shows the parameter relation during the display of the three-dimensional image, and shows the relation with the observing eyes with a three-dimensional display which effects three-eye display as an example. The display size is defined as $W_0$, the supposed observation distance is defined as $Li0$, and the observation base length is defined as K. To display a three-dimensional image of a natural three-dimensional feeling, the distance between the radioactive ray sources and the light receiving surface and the size of the light receiving surface are adjusted so as to satisfy the following relation:

$$\frac{\text{observation base length }(K)}{\text{radioactive ray source interval }(\Delta x)} \times \frac{\text{supposed observation distance }(Li0)}{\text{distance between radiaton source and light receiving surface }(L)} \times \frac{\text{size of light receiving surface }(W)}{\text{size of diplay surface }(W_0)} = 1 \quad (1)$$

The distance between the radioactive ray source and the light receiving surface should be the distance between the radioactive ray source and the object to be photographed, but the object to be photographed is considered to be substantially in close contact with the light receiving surface and therefore, the latter distance can be approximated to the distance between the radioactive ray source and the light receiving surface. The size of the light receiving surface is the size on the light receiving surface corresponding to the view field displayed on the three-dimensional display, and the distance between the radiation source and the light receiving surface is the projection distance between the radioactive ray source and the light receiving surface. That is, when the zoom ratio of the three-dimensional display parameters changes, the size of the light receiving surface changes. In a case where the interval between the radiation sources is determined with the three-dimensionality parameter and the display three-dimensionality limit range taken into consideration, the interval between the radioactive ray sources is calculated so as to depart from the relation of the expression (1).

$$\frac{\text{observation base length }(K)}{\text{radioactive ray source interval }(\Delta x)} \times \quad (2)$$
$$\frac{\text{supposed observation distance }(Li0)}{\substack{\text{distance between radiaton surface} \\ \text{and light receiving surface }(L)}} \times$$
$$\frac{\text{size of light receiving surface }(W)}{\text{size of diplay surface }(W_0)} = \times$$
$$\text{three-dimensionality coefficient} = 1$$

The three-dimensionality coefficient, when the display three-dimensionality limit range is not taken into consideration, is a coefficient representative of the three-dimensionality parameter, and a case where coefficient=1 corresponds to a natural three-dimensional feeling. If the coefficient >1, observation is done at a similar supposed observation distance and display surface size, and when the distance between the radiation source and the light receiving surface and the size of the light receiving surface are not changed, the radioactive ray source interval is increased as the result, and the presented parallax amount becomes great and the three-dimensional feeling is emphasized. If conversely, the coefficient <1 under a similar condition, the radioactive ray source interval is narrowed and the three-dimensional feeling is weakened.

When the display three-dimensionality limit range is taken into consideration, the radiation source interval is calculated so as not to exceed the display three-dimensionality limit range, i.e., the limit of the presentable parallax of the three-dimensional display. As compared with the allowable amount limited by the image fusion limit of the human eyes, the conventional three-dimensional display is very narrow in the display three-dimensionality limit range and therefore, in many cases, the interval between the radioactive ray sources, i.e., the three-dimensional feeling of the displayed three-dimensional image, is limited by this limit range. Assuming that a coefficient for considering the display three-dimensionality limit range parameter is a three-dimensionality limiting coefficient, $$\frac{\text{observation base length }(K)}{\text{radioactive ray source interval }(\Delta x)} \times \quad (3)$$
$$\frac{\text{supposed observation distance }(Li0)}{\substack{\text{distance between radiaton source} \\ \text{and light receiving surface }(L)}} \times$$
$$\frac{\text{size of light receiving surface }(W)}{\text{size of diplay surface }(W_0)} = \times$$
$$\text{three-dimensionality coefficient} \times$$
$$\text{three-dimensionality limiting coefficient} = 1.$$

The display three-dimensionality limit range parameter is basically represented by a parallax amount on the display surface corresponding to a maximum amount of jumping-out and amount of sinking capable of being displayed on the three-dimensional display. There is also possible a case where the display three-dimensionality limit range parameter is represented in the form of the parallax amount between the adjacent view point images of the three-dimensional image when the maximum jumping-out and sinking are displayed.

In this case, by the use of the image step number parameter incident on the observing eye when observation is effected at the supposed observation distance, the display three-dimensionality limit range parameter can be converted into a value corresponding to the relation between adjacent images based on a parallax amount corresponding to parallax images incident on the right and left eyes at the supposed observation distance. Further, by the use of the relation between the image step number parameter incident on the observing eye when observation is effected at the supposed observation distance and the parameters of the display size and the size of the light receiving surface, display three-dimensionality limit range parameter can be also converted into the form of the value of the parallax amount between parallax images obtained by being photographed by arbitrarily supposed two radioactive ray sources and the light receiving surface.

Then, by the use of the distance between the radioactive ray sources and the light receiving surface, the size of the light receiving surface and the radiation source interval calculated with the three-dimensionality parameter taken into consideration, the three-dimensionality limiting coefficient is determined so that the range of the display parallax amount calculated relative to the presence range of the object to be photographed or the parallax amount range between parallax images obtained by the radioactive ray source position and the light receiving surface may not exceed the parallax amount calculated above.

Figure 7:
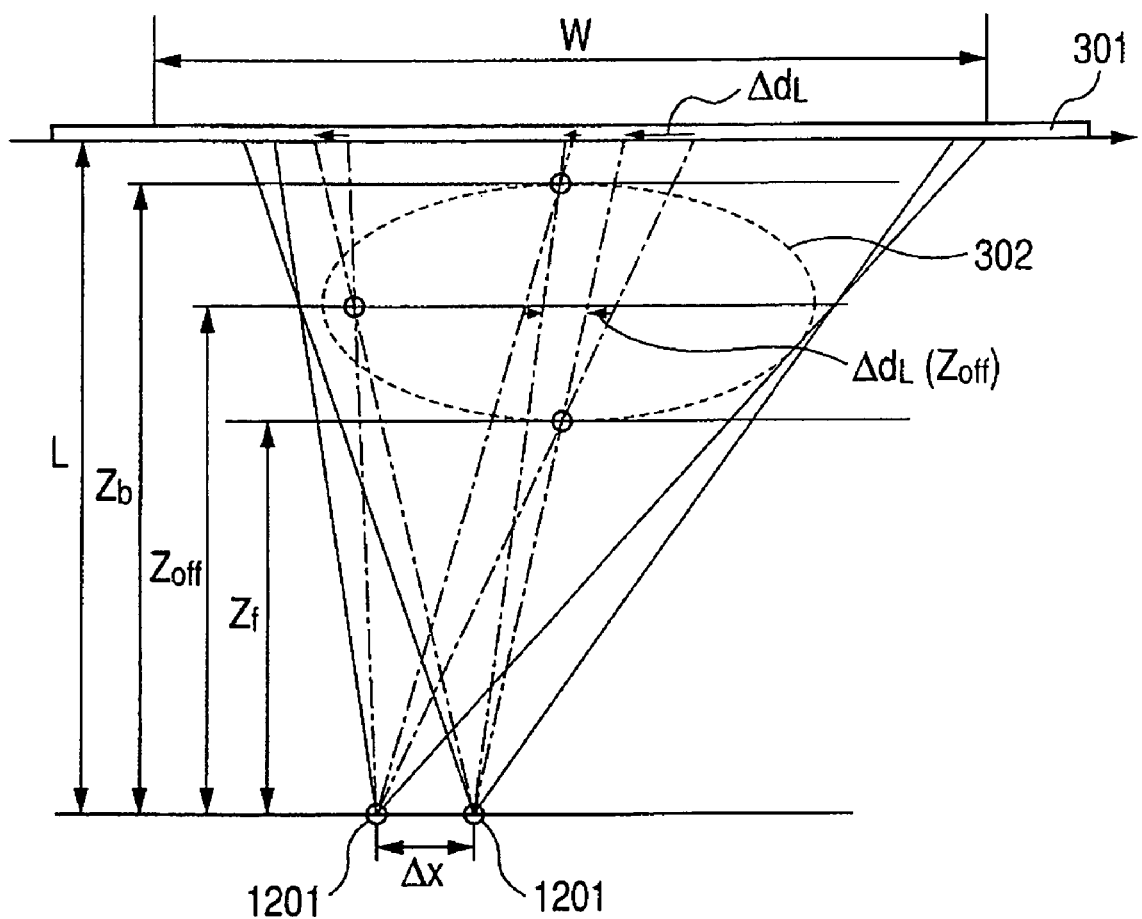
FIG. 7 illustrates the amount of parallax on the light receiving surface of the three-dimensional image pickup and display apparatus according to Embodiment 1 of the present invention.

The presented parallax amount at this time is found as follows. FIG. 7 illustrates the parallax amount on the light receiving surface obtained when the object to be photographed is photographed by the photographing apparatus. The reference numeral 1201 designates two supposed radioactive ray sources, the reference numeral 301 denotes the light receiving element, and the reference numeral 302 designates the object to be photographed.

The following mathematical expression is an expression for calculating a parallax amount $\Delta_{dL}$ at the light receiving surface distance L of the light receiving element 301. Z is a distance perpendicular to the light receiving surface from the radioactive ray source to a space point constituting the object to be photographed.

$$\Delta_{dL}(Z) = \left(\frac{L}{Z} - 1\right)\Delta x \quad (4)$$

Thus, the parallax amount can be found from the geometrical relation among the radioactive ray source interval $\Delta x$, the distance L between the radioactive ray source and the light receiving surface, and the distance Z. The size of the light receiving surface, as described above, represents not the size of the actual light receiving surface, but the size of a light receiving surface by which the image used for three-dimensional display is photographed.

Also, the range of the display parallax amount calculated relative to the presence range of the object to be photographed can be changed by adjusting the relation between the distance between the radioactive ray source and the light receiving surface and the size of the light receiving surface by image shift and magnifying process. The following expression represents the parallax amount of parallax images obtained when an imaginary light receiving surface is set at a distance $Z_{off}$ from the radiation source.

$$\Delta dZ_{off}(Z) = \left(\frac{Z_{off}}{Z} - 1\right)\Delta x = \left(\frac{Z_{off} - Z}{Z}\right)\Delta x \qquad (5)$$

Also, the parallax amount $\Delta d'$ between images, which is obtained by applying to the parallax image the image shift rendering the parallax amount $\Delta dL\,(Z_{off})$ on the light receiving surface at a distance L corresponding to the space point at the distance $Z_{off}$ from the radiation source and a magnification change of $Z_{off}/L$, satisfies the following expression, in contrast to the above-mentioned mathematical expression (5).

$$\begin{aligned}\Delta d'(Z) &= \frac{Z_{off}}{L}\{^\Delta d_L(Z) - {}^\Delta d_L(Z_{off})\} \qquad (6)\\ &= \frac{Z_{off}}{L}\left\{\left(\frac{L}{Z} - 1\right)\Delta x - \left(\frac{L}{Z_{off}} - 1\right)\Delta\right\}x\\ &= \frac{(Z_{off} - Z)}{Z}\Delta x.\end{aligned}$$

By applying shift processing and a magnification change to the images as described above, it becomes possible to obtain a parallax amount obtainable between the parallax images when the relation between the distance between the radioactive ray source and the light receiving surface and the size of the light receiving surface is changed. Thus, the image shift and magnification change between the parallax images become processing useful to efficiently suppress the range of the presented parallax amount to the display three-dimensionality limit range.

Next, the intervals among all radioactive ray sources are determined. The interval in the case of regular intervals can be calculated from the radiation source interval calculated between two radioactive ray sources corresponding to the parallax images incident on the right and left eyes at the supposed observation distance, and the relation of the image step number incident on the observing eye when observation is effected at the supposed observation distance. Usually, the intervals are set to regular intervals. However, when three-dimensional display is to be effected in imitation of vergence viewing, the intervals are calculated at irregular intervals with a geometrical relation taken into consideration.

After the parallax amount has been obtained, lastly the positions and emission directions of the radioactive ray sources are determined. The positions and emission direction of the radioactive ray sources are determined so that in conformity with any change in the positions of the radioactive ray sources, radiation may be efficiently applied to the object to be photographed, and may be efficiently received by the light receiving surface. In other words, for example, the emission directions can be set so as to locate the center of vergence at the centroid position of the object to be photographed, and the positions of the radioactive ray sources can be set so as to be rightly opposed to the object to be photographed.

Also during photographing, the light receiving surface may be horizontally shifted symmetrically about the object to be photographed with respect to the light emitting positions of the radioactive ray sources. That is, the emission directions may be determined so that the central axes of the emission directions may cross each other at the position of observation of the object to be photographed so that the object to be photographed may be efficiently photographed with all parallax images, and the light receiving surface may be shifted so as to efficiently receive the transmitted light from the object to be photographed. Then, if any change occurs to the three-dimensional display parameters, the number of light emission, the light emitting positions and the light emission intervals and directions of the radioactive ray sources are changed.

Next, the determination of the positions and directions of the radioactive ray sources taking the three-dimensional display parameters in the display mode B (FIG. 6B) into consideration is effected. The display mode B is an image obtained by mirroring process the display mode A, and is not changed in the presented parallax amount. Accordingly, in the display mode B, the determination of the positions and directions of the radioactive ray sources which are light sources is effected from the display parameter in the same manner as in the display mode A.

Description will now be made of a method of determining the positions of the radioactive ray sources during transmission image photographing for generating a three-dimensional image taking the display parameters in the display mode C into consideration. Description will be made here of such a method of calculating the base length of imaginary view point images constituting the three-dimensional image of an opposite view point that a natural three-dimensional feeling is obtained in a case where the characteristic of a three-dimensional display which displays is known in advance and observation is effected at the supposed observation distance which is the preferable observation distance of this three-dimensional display, and the calculation of the optimum interval and range of the radioactive ray source positions during photographing for generating the imaginary view point images.

The natural three-dimensional image displayed on the three-dimensional display is indicative of a three-dimensional image in which the ratio between the amount of jumping-out and the amount of sinking by the displayed size of a content object on the display surface and the parallax about the object is the same as that of an actual object.

Also, for simplification of description, it is to be understood that the aspect ratio of the three-dimensional display and the aspect ratio of the image pickup surface are equal to each other and at one to one magnification, and any processing concerned with the changing of the angles of view for zoom, slitting, etc. is not effected on the photographed image, but the entire area is intactly displayed. Actually, in a case where an attempt is made to obtain a natural three-dimensional image when there are differences and changes among these three-dimensional display parameters, in the calculation of the base length of the imaginary view point image, the adjustment of the size of the light receiving surface or the size of the display surface is effected as in the display mode A to thereby calculate the base length of the imaginary view point image with the relation of the ratio between the sizes of the image pickup surface and the light receiving surface taken into consideration. Also, it is to be understood that the resolution of the photographed transmission projection image is sufficiently high relative to the resolution of the imaginary view point image.

Figure 8:
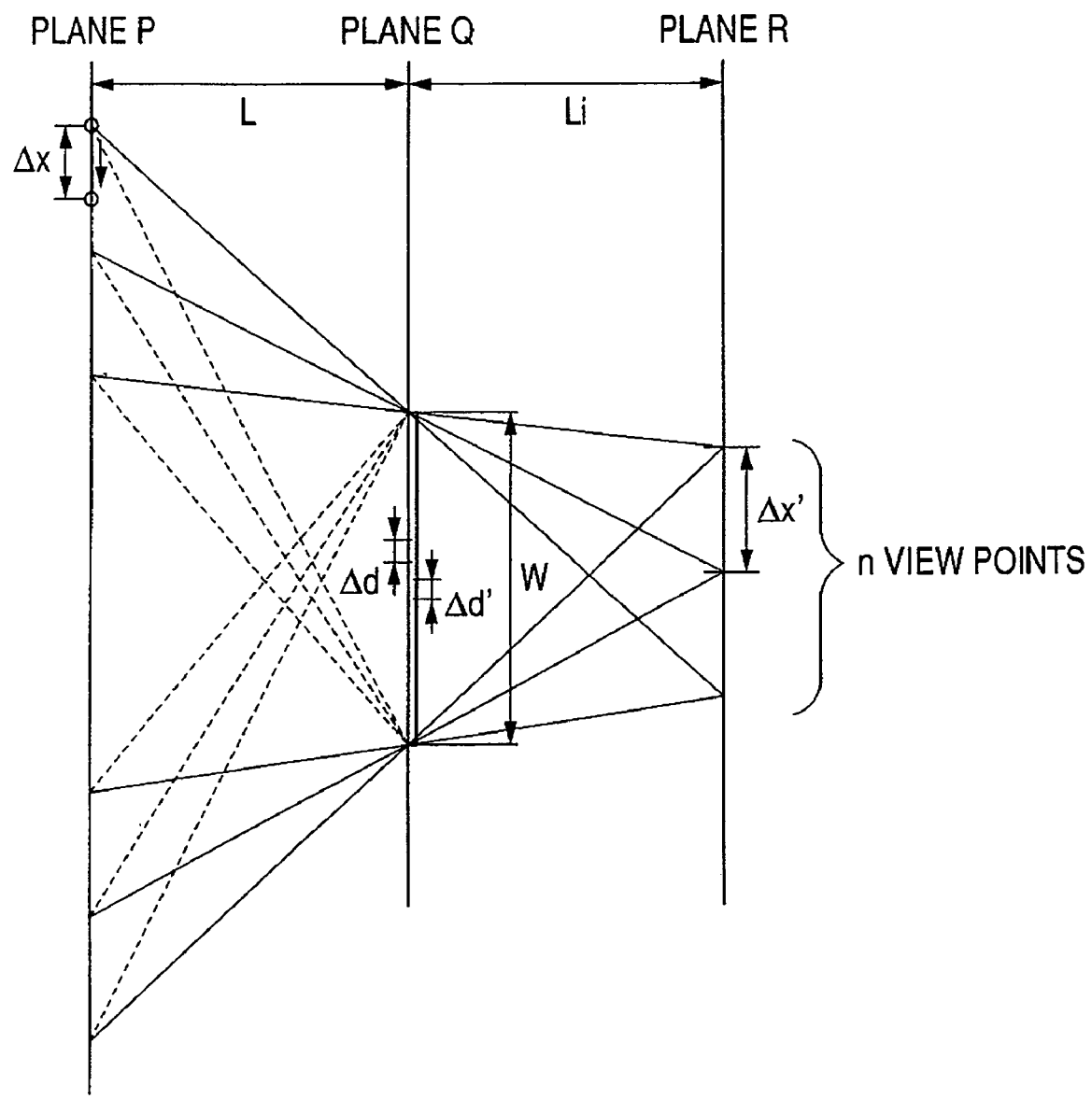
FIG. 8 illustrates the relation of three-dimensional display parameters regarding the image conversion processing of the three-dimensional image pickup and display apparatus according to Embodiment 1 of the present invention.

Description will first be made of the calculation of the base length of the imaginary view point image for observing a natural three-dimensional image. FIG. 8 shows a relation in which the view points are disposed on the basis of the geometrical relation between the photographed transmission image and the displayed three-dimensional image on the three-dimensional display, and in accordance with the condition of the equivalent relation between the zoom in the transmission image photographing device of FIG. 4A and the three-dimensional image display device of FIG. 4B and the display and light receiving surfaces.

In FIG. 8, the three-dimensional display parameters are set. The supposed observation distance of the three-dimensional display is defined as Ls, and the size of a horizontal display surface is defined as Ws. As the result, the horizontal display view angle can be represented as $\phi s = Ws/Ls$.

Next, from the size Wi of a horizontal image pickup surface and an observation distance Li which is the distance between the radioactive ray sources and the light receiving surface, the horizontal photographing view angle can be represented as $\phi i$. While the horizontal view angle is used here, use may also be made of a vertical or diagonal view angle.

To display a natural three-dimensional image free of distortion when the supposed observation distance Ls, the size Ws of the horizontal display surface and the size Wi of the horizontal image pickup surface are fixed, the imaginary observation distance Li is adjusted so that the imaginary observation view angle $\phi i$ may simply become equal to the display view angle $\phi s$. Or it becomes possible by adjusting the photographing base length. Assuming that the number of the observing eye incident image steps is 1 (that is, an adjacent image is incident on the observing eye), when $\phi s$ and $\phi i$ are equal to each other, an imaginary view point base length $\Delta x'$ becomes an image pickup base length, i.e., the inter-eye distance $\Delta x' = K = 65$ [mm]. As the result, from the geometrical relation between an angle of view for obtaining a natural three-dimensional feeling and the base length, the interval between the radioactive ray sources satisfies the following equation.

$$\frac{\varphi s}{\varphi i} = \frac{K}{\Delta x}. \quad (7)$$

Usually, the image step number is not always limited to 1 and therefore, assuming that the image step number is s, the base length between adjacent imaginary view point images for generating a natural three-dimensional image in $\Delta x' = K/s$ and likewise, the interval between adjacent radioactive ray sources taking the view angle relation between display and image pickup and the observing eye incidence step number into consideration is represented by $$\Delta x' = \frac{K}{s}. \quad (s:\text{step number}) \quad (8)$$

Thus, the imaginary view point position at the base length at the imaginary view point is obtained, and such an ideal distance $L_{i\_ideal}$ between the radioactive ray source and the light receiving surface as intersects with a ray of light from other imaginary view point position through all pixels on the light receiving surface is represented by $$L_{i\_ideal} = \frac{n \cdot \Delta d}{\Delta x' - n \cdot \Delta d} Ls. \quad (n = 1, 2, \ldots) \quad (9)$$

Figure 9:
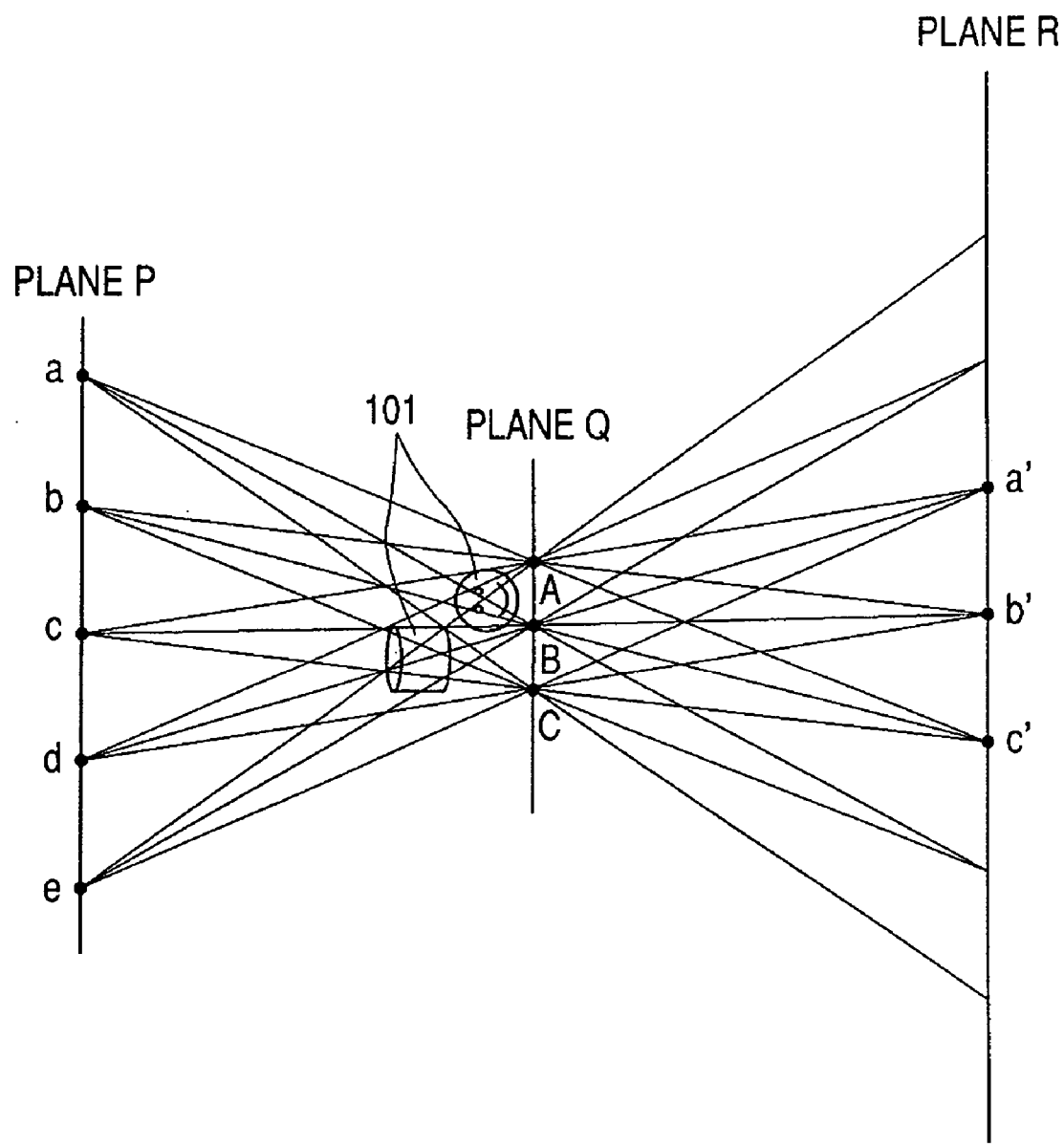
FIG. 9 illustrates the relation between the transmission image according to Embodiment 1 of the present invention and the transmission image after view point conversion processing.

In a case where the ideal distance between the radioactive ray source and the light receiving surface can be provided, when as shown in FIG. 9, an attempt is made to obtain the pixel data of a certain arbitrary pixel from a plurality of imaginary view point positions, image data can be obtained from images at one and the same radioactive ray source position.

In FIGS. 8 and 9, a plane P is the position of the actual radioactive ray source, a plane Q is the light receiving surface, and a plane R is an imaginary view point position, and the interval between the radioactive ray sources on the plane P is determined by the relation of the above-mentioned expression, and Li is appropriately set in accordance with the pixel interval on the plane Q. Also, on the basis of the geometrical relation, rays of light from the radiation sources emitted from all the set imaginary view points on the plane R pass through all pixels on the plane Q, and come to intersect with any one radioactive ray source position on the plane P.

However, the imaginary observation distance which is the distance between the radioactive ray source and the light receiving surface cannot secure its adjustment range so well and therefore, Li is set to the closest Li of the adjustable distances between the radioactive ray sources and the light receiving surface. As regards the value of the closest Li, by the use of a distance Li' as a schematic value, a corresponding order number is found by $$n_{int} = INT\left(\frac{Li'}{Ls + Li'} \cdot \frac{\Delta x'}{\Delta d}\right), \quad (10)$$

and Li which satisfies $n = n_{int}$ or $n = n_{int} + 1$ is selected. Here, INT( ) is a function which rounds a real number value in ( ) to an integer value close to 0.

Then, relative to Li set by the geometrical relation of mathematical expression (10), the base length of the radioactive ray sources is calculated by $$\Delta x = \frac{WiLs}{WsLi}\Delta x'. \quad (11)$$

Thereby, the appropriate base length of the radioactive ray sources is calculated.

Figure 10:
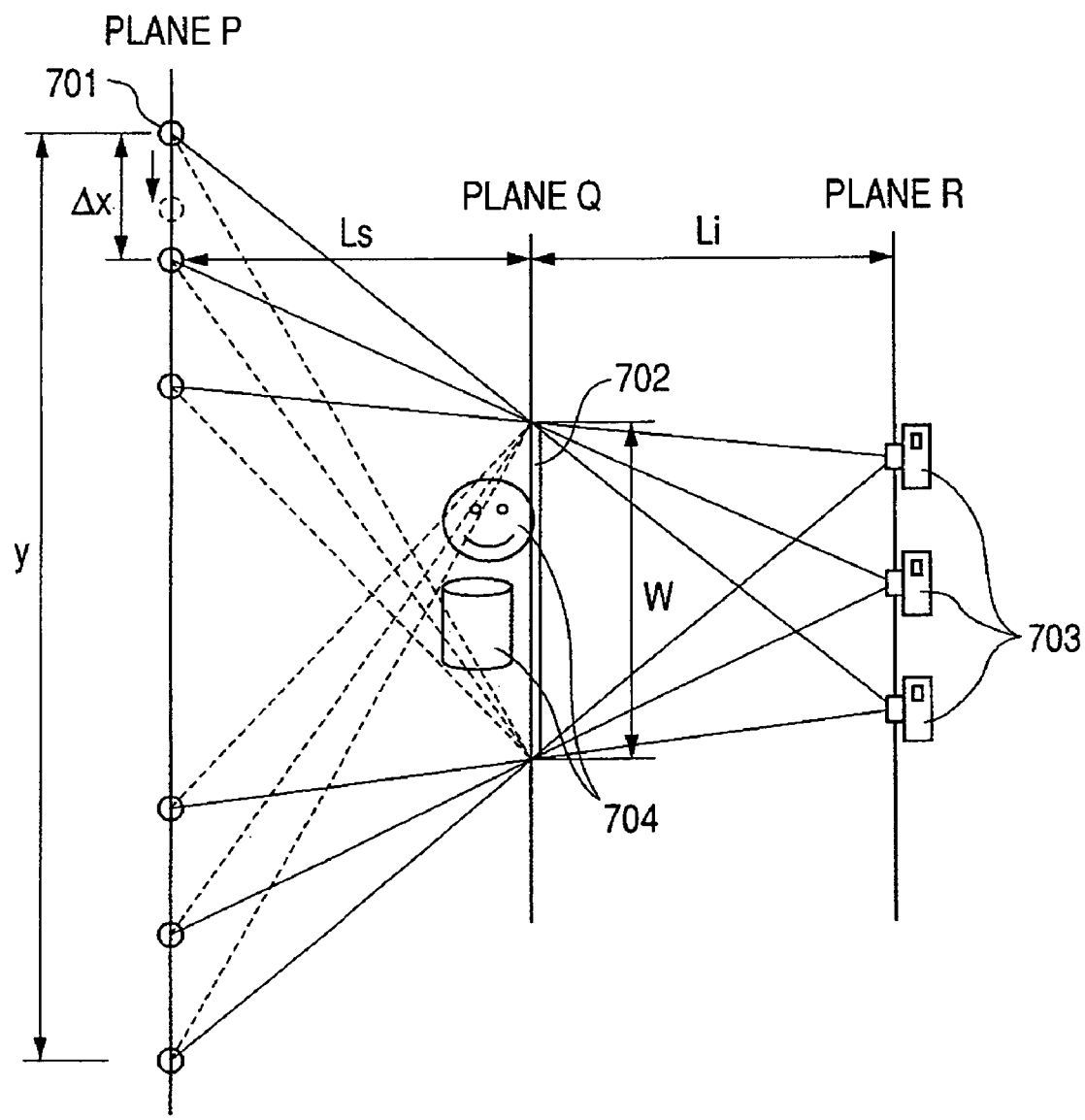
FIG. 10 illustrates the relation between a radiation source position according to Embodiment 1 of the present invention and an imaginary view point.

The radiation source (light source) range, as shown in FIG. 10, is set so as to arrange the radioactive ray sources at the radioactive ray source intervals within a range to which straight lines passing through the imaginary view points and both of outermost angles of the image pickup surface reach on the plane P. In the case of such a relation between the image pickup surface and the imaginary view point as shown in FIG. 10, when the distance from the central axis to the outermost angle imaginary view point position is defined as x and the imaginary observation distance is defined as Ls, and the interval between the image pickup surface and the radioactive ray sources is defined as Li, and the size of the horizontal image pickup surface is defined as Wi, and the light source range is defined as y, the light source range y can be defined by the following expression, $$y = \frac{Li}{Ls}x + \left(1 + \frac{Li}{Ls}\right)Ws. \quad (12)$$

Also, the light source range in the vertical direction can likewise be defined, and the radioactive ray source light emitting positions can be set at the radioactive ray source interval Δx within the range of the light source range y, and the light source range for photographing a radioactive ray transmission image which is the original data can be determined. Thus, the radioactive ray source interval and range on the plane P can be determined.

<Photographing Process (Step 404)>

At this step 404, in conformity with the radioactive ray source positions and directions determined on the basis of the display mode and the three-dimensional display parameters, the radioactive ray sources are caused to emit light a calculated number of times, and the transmission images of the object to be photographed are successively photographed in a time sharing fashion by the light receiving element. Also, basic processing such as gradation conversion processing and sharpening process resulting from the photographing operation is effected on the photographed image.

<Image Data Save Processing (Step 405)>

At this step 405, images corresponding to a plurality of view points photographed at the step 404 are stored in a fixed memory medium such as the mass storage device 2022. The plurality of stored images are used for three-dimensional image generation, and are also used for being observed as ordinary two-dimensional radioactive ray transmission images, and for a purpose relating to arbitrary view point image generation. In this saving process, design may be made to effect processing after confirming the save of the images.

<Image Conversion Processing (Step 408)>

Next, image (view point) conversion processing conforming to the display mode set at the step 402 (and the three-dimensional display parameters obtained at the step 401) is effected on the plurality of images photographed at the step 404.

First, in the display mode A, the view point conversion processing of the transmission images is not effected, but such a three-dimensional image as will be described later is generated from the plurality of images. In the case of the display mode B, mirroring process is effected on the photographed transmission images, but as in the display mode A, the view point conversion processing is not effected.

Subsequently, in the display mode C, view point conversion processing shown below is carried out on the plurality of photographed images.

Description will hereinafter be made of conversion processing for generating, in the display mode C, such a multi-view point image necessary to display a three-dimensional image on the three-dimensional display with the plurality of photographed images as an input as has been photographed from a view point on a side opposite to the radioactive ray sources with the view angle of the light receiving surface as a photographing angle. The generation of the image at the imaginary view point position determined at the light source position and direction changing step of the step 404 is effected. Also, when the emphasis or attenuation of the three-dimensional feeling is to be done, the imaginary view point position is further changed so that the base length may change.

FIG. 10 is a typical view representing a radioactive ray source 701, a light receiving surface 702 and the imaginary view point position of an image generated by view point conversion processing, and shows the relation between a photographing device 703 and an object to be photographed 704.

Figure 11:
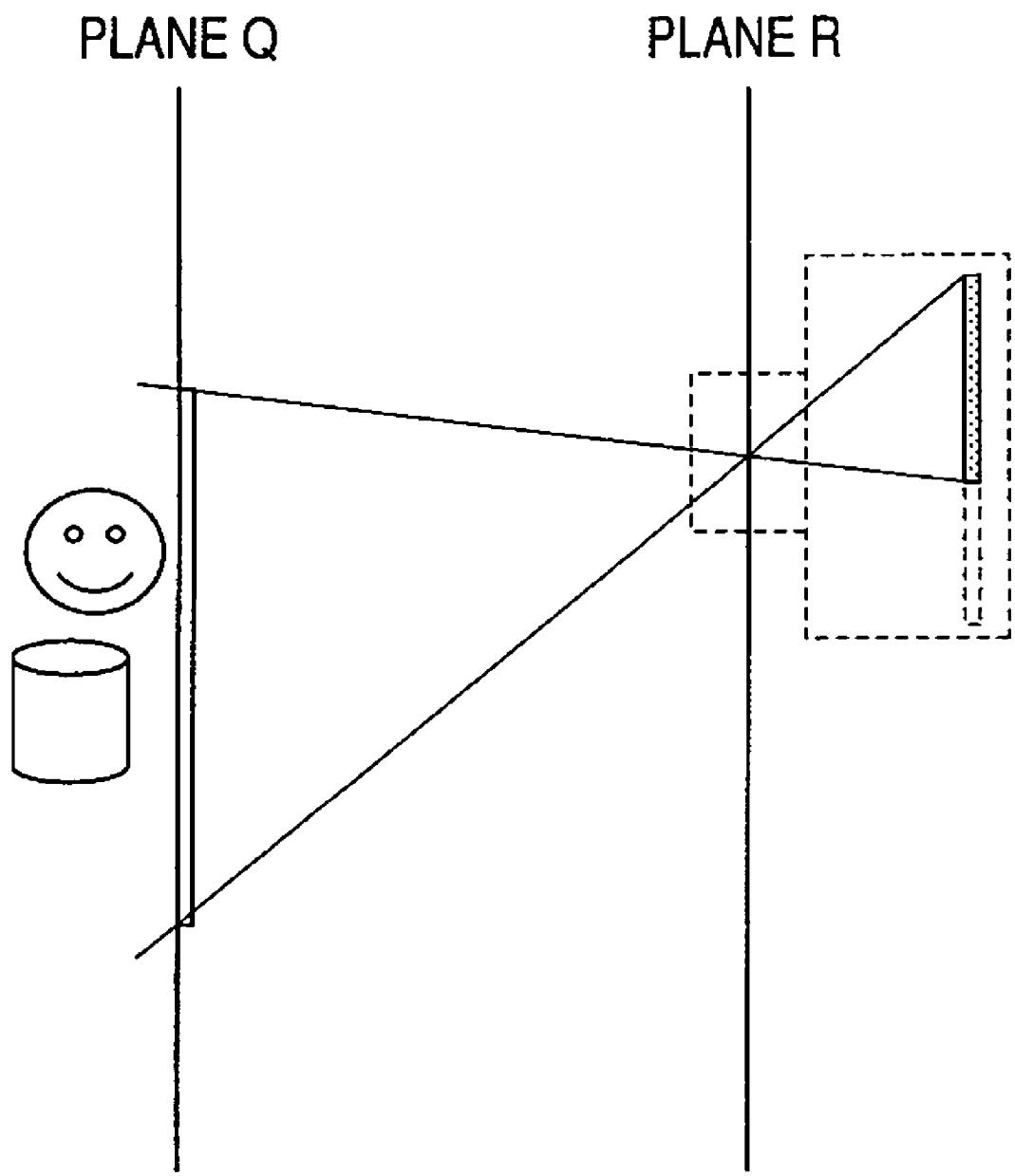
FIG. 11 illustrates the relation between the light receiving surface according to Embodiment 1 of the present invention and the imaginary image plane of an imaginary view point image.

First, the radioactive ray source position is sequentially moved, and an imaginary view point image at an imaginary view point position is generated by the use of the information of a plurality of images obtained at the light receiving surface position. It is to be understood that the view angle of the generated imaginary view point image, as shown in FIG. 11, is the same as a view angle at which the light receiving surface is viewed from the imaginary view point position. Also, for the simplification of description, it is to be understood here that the watching point is the center of the light receiving surface position and is in a distortion-corrected positional relation. FIG. 10 shows an example in which three imaginary view points are taken in the horizontal direction, and three imaginary view point images are generated from an image.

It is to be understood that the aspect ratio is the same between the imaginary view point image generated by conversion processing and the displayed image on the three-dimensional display and further, the observation view angle supposed by effecting the cutting-out of the displayed image on the three-dimensional display and the addition of a surplus area is not changed. This is because if the view angle during display (observation view angle: the relation between the display size and the observation distance) is changed from a view angle supposed during conversion image generation, the three-dimensional feeling will change.

The movement plane of the radioactive ray source 701 is defined as a plane P, the light receiving element 702 is defined as a plane Q, a photographing device indicative of the generated imaginary view point image and the view point position thereof is defined as a camera 703, and the plane on which the view point position exists is defined as a plane R.

First, as shown in FIG. 8, a parameter concerned in conversion processing is set. The number of imaginary view points is defined as n, the distance between the imaginary view points and the light receiving surface of the light receiving element 702 is defined as Li, the base length between the imaginary view points is defined as Δx', the distance between the radioactive ray source and the light receiving surface is defined as L, the size of the light receiving surface is defined as W, and the pixel pitch of the light receiving surface is defined as Δd. Also, the pixel pitch of the imaginary view point image when an image is projected from the imaginary view point image through a view point position on the plane R is defined as Δd', and the size of the image likewise projected is defined as W'. The size and aspect ratio of the image when the light receiving surface and the imaginary view point image are projected onto the light receiving surface position through the imaginary view point as described above are the same (W=W'), and the pixel pitches are also the same (Δd=Δd').

FIG. 12B, like FIG. 12A, is an illustration when R (x1, y1) is defined as an imaginary view point, and the data of a certain pixel Q (il, jr) (1≦l≦w, 1≦rh) when the extraction of image data is sequentially effected is extracted. As in the case of FIG. 12A, consider a ray of light emerging from an imaginary view point R (x1, y1) and passing through the pixel Q (il, jr) of the imaginary view point image, and image data is extracted from a radiation projection image having a point P (x', y') at which the ray of light is extended and intersects with the plane P as a radioactive ray source position.

In FIGS. 12A and 12B, the pixel data of the Q (il, jr) position in the radiation projection image having P (x', y') as the radioactive ray source position is extracted as the image data of the pixel Q (il, jr) in the imaginary view point image.

The extraction of the image data is sequentially effected, and if all the pixel data of an imaginary view point image having R (x1, y1) as an imaginary view point can be extracted, an imaginary view point image corresponding to the next imaginary view point position R (x2, y2) is generated.

FIG. 12C shows the manner in which a certain pixel Q (i1, j1) constituting an imaginary view point image corresponding to the next imaginary view point position 802, R (x2, y2) is extracted from the pixel data of a plurality of images. Consider a ray of light emerging from the imaginary view point R (x2, y2) and passing through Q (i1, j1). This Q (i1, j1), if extended when it is at the same position as the pixel position extracted in FIG. 12A, passes through a point P (x", y") at which it intersects with the plane P.

However, P (x", y") becomes a position different from P (x, y), and the image data of another radioactive ray image differing in radioactive ray position is extracted. About the remaining pixels constituting the imaginary view point image having R (x2, y2) as the view point, the extraction of image data is likewise sequentially effected to thereby generate an imaginary view point image. Then, imaginary view point images corresponding to the remaining view point positions R (x2, y2), . . . , R (xn, yn) are likewise generated.

Figure 13A:
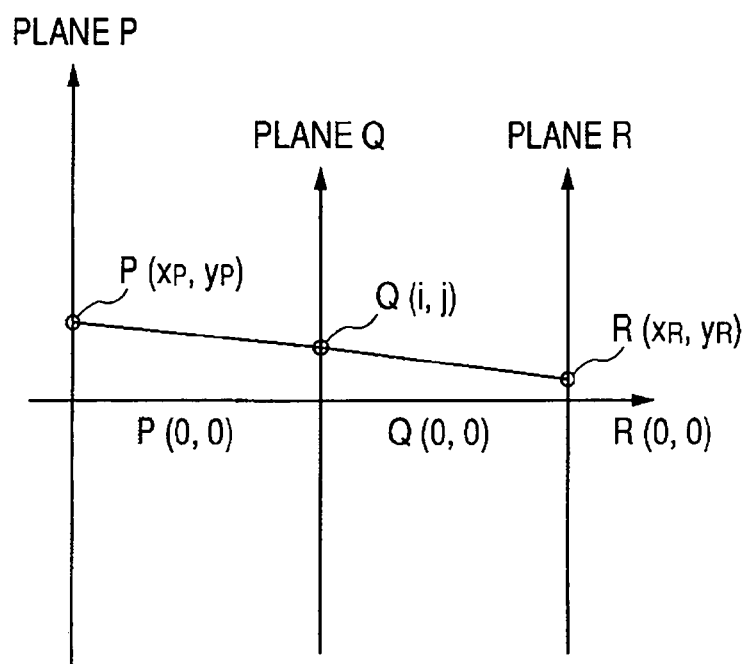
FIGS. 13A and 13B illustrate a coordinates system in the image conversion processing according to Embodiment 1 of the present invention.
Figure 13B:
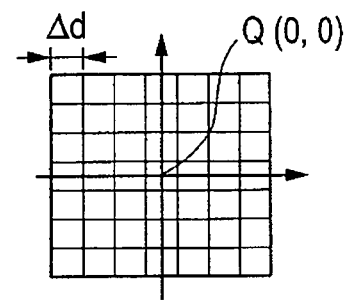

In the calculation of the radioactive ray source position, such a coordinates system as shown, for example, in FIGS. 13A and 13B is set, and the radioactive ray source position is calculated from the imaginary view point R (x, y) and the pixel position Q (i, j). When the coordinates system as shown in FIGS. 13A and 13B is set, $$P(x_p, y_p) = \left[(i \cdot \Delta d - x_R)\frac{L+Li}{Li}, (j \cdot \Delta d - y_R)\frac{L+Li}{Li}\right]. \quad (13)$$

The procedure of generating an image at an imaginary view point 801 generated by view point conversion processing will now be described with reference to FIGS. 12A to 12C.

FIG. 12A shows the manner in which the data of a pixel Q (i1, j1) constituting an imaginary view point image having R (x1, y1) on the plane R as an imaginary view point is extracted. When a ray of light emerging from the imaginary view point R (x1, y1) and passing through Q (i1, j1) is considered and this is extended, it passes through a point P (x, y) at which it intersects with the plane P. From a geometrical relation, the pixel Q (i1, j1) in a radioactive ray projection image having this point P (x, y) as a radioactive ray source position is extracted as the image data of a pixel Q (i1, j1) in an imaginary view point image having R (x1, y1) as an imaginary view point. The pixel extraction processing as described above is sequentially effected in the form of Q (i1, j1), Q (i2, j1), . . . , Q (il, jr), . . . , Q (iw, jh) about all the pixels of the imaginary view point image having R (x1, y1) as the imaginary view point. Then, a pertinent radioactive ray source position is geometrically primarily calculated.

FIG. 13A represents the relation between the setting of the coordinates axes in the plane P, the plane Q and the plane R and a radioactive ray source position R (xP, yP) corresponding to an imaginary view point R (xR, yR) and an extracted pixel position Q (i, j). FIG. 13B is a view of the plane Q as it is seen from the plane R side, and the pixel at the optical axis position is the origin of the coordinates, and the pixel size is Δd.

When there is not a transmission image at a radioactive ray source position P (x, y) at the extraction of pixel data, the pixel data of a pixel corresponding to a transmission image having a radioactive ray source position at the nearest point is utilized, or the interpolation by the pixel data of the pertinent pixel position of a transmission image having radioactive ray source positions at a plurality of nearby points is effected to thereby obtain pixel data.

In this conversion processing, processing is effected with the view angle (the size of the display screen/observation distance) and the base length taken into consideration. The parameters of this view angle (the size of the display screen/observation distance) and the base length are parameters which should be considered in order to express a natural three-dimensional feeling on the three-dimensional display. If there is a difference in the relation between the displayed image on the three-dimensional display and the number of pixels of the transmission image, or between the display surface size of the three-dimensional display and the light receiving surface size of the transmission image, consideration is given when the view point position of the imaginary view point image is prescribed.

When interpolation processing is not effected during the extraction of the pixel data, that is, when it is possible to provide an appropriate distance between the light receiving surface and the radioactive ray source which satisfies the equation (9), the generation of an image of a high quality becomes possible. This becomes possible by setting the radioactive ray source position so that a ray of light passing through the pixels on all display surface images may intersect with the radioactive ray source position, in accordance with the information of the imaginary view point position.

FIG. 9 shows these relations. P represents a radioactive ray source plane on which the radioactive ray source is disposed, and R represents an imaginary view point plane on which the imaginary view point is disposed. The plane Q on the plane P side represents the light receiving surface, and the plane Q on the plane R side represents the display surface, and it is to be understood here that the size of the light receiving surface and the size of the image surface are the same, and the sizes of the respective pixels are also the same. In FIG. 9, there is shown a relation in which the photographing distance and the supposed observation distance are equal to each other.

Letters A, B and C on the plane Q represent the positions of pixels. By determining imaginary view point positions a', b' and c' on the plane R, it is possible to effect view point conversion processing without effecting interpolation from a geometrical relation as in FIG. 9 if the supposed observation distance (the interval between the plane R and the plane Q) and the ratio between the size of the displayed image and the size of the photographed image is considered with a result that the image pickup surface pixel interval is sufficiently narrow as compared with the display surface pixel interval. Therefore, radioactive ray source positions a, b, c, d and e on the plane P can be determined.

Accordingly, if such radioactive ray source positions are set in the radiation source position and direction changing processing of the step 403, all pixel data at the extraction of any pixel data of a view point conversion image having any view point position on the plane R exist as the pixel data of the photographed radioactive ray transmission image and therefore, basically without effecting a high degree of interpolation processing, it becomes possible to generate an image of a high quality by only adding simple processing such as smoothing.

When it is desired to strengthen the three-dimensional feeling during the display of a three-dimensional image, the distance between the imaginary view points of the imaginary view point image (the base length) can be widened, and when it is desired to weaken the three-dimensional feeling during the display of the three-dimensional image, the distance between the imaginary view points (the base length) can be narrowed.

<Three-Dimensional Image Generating Processing (Step 407)>

Next, with transmission images corresponding to a plurality of view points and images generated while being subjected to the view point conversion processing at the step 406 as input data, a three-dimensional image conforming to the characteristic of the three-dimensional display, in other words, the pixel arrangement of the three-dimensional display, is generated. In this three-dimensional image generating processing, a three-dimensional image is synthesized and generated by multiplex processing which samples a pixel from each view point image (see Japanese Patent Application Laid-Open No. 2003-209858), but three-dimensional image generating (synthesizing) processing conforming to the characteristic of the three-dimensional display effecting three-dimensional display can be effected.

<Display Processing (Step 408)>

Next, the three-dimensional image based on the transmission image generated at the step 407 is displayed on the three-dimensional display. Also, in this display processing, when instead of displaying an image on the three-dimensional display 206, the image is to be outputted as a printed matter by the use of the printer 207, in any of a case where the image is directly printed on an optical element like a lenticular sheet or an integral photometric (IP) sheet and a case where the image is printed on a printing medium presenting a three-dimensional image in combination with these optical elements, the processing of the step 401 and subsequent steps is newly effected to set three-dimensional display parameters adapted to the above-mentioned optical elements, thereby generating a three-dimensional image. By thus processing, a three-dimensional image better than when the three-dimensional image generated on the three-dimensional display in conformity with suitable three-dimensional display parameters is directly printed is obtained.

As described above, the transmission image photographing device 201 in the present embodiment changes the positions of the radiation sources in conformity with the three-dimensional display parameters of the three-dimensional display 206 and effects the photographing of the transmission images. Accordingly, when a three-dimensional image (three-dimensionally viewable image) generated from the transmission images is to be displayed on the three-dimensional display 206, it can be made possible to reproduce the recognition of the size and positional relation of a noted region free from distortion peculiar to a transmission image and obtained from the three-dimensional image as well as the actual positional relation.

In other words, it is possible to eliminate the problem that heretofore, because of being a transmission image, all the information of that region of an object to be observed through which a radioactive ray has been transmitted is superposed, and it is difficult to accurately grasp the distribution of a particular region (sick region) on a three-dimensional space. Therefore, the perception of the three-dimensional disposition in the transmission image becomes easy, and it becomes possible to provide a three-dimensional image conforming to the observer's intention.

Also, the three-dimensional image pickup and display apparatus according to the present embodiment effects view point conversion processing conforming to the three-dimensional display parameters on transmission images at a plurality of photographed radiation source positions to thereby actually obtain a transmission image from an imaginary radiation source position, i.e., an imaginary view point position. Therefore, it is possible to generate and display a three-dimensional image by a suitable transmission image which does not cause misperception or the like due to the distortion that that side of the object to be photographed which is near the light receiving surface is displayed small and the side existing afar is displayed large which poses a problem in the three-dimensional display of a radioactive ray transmission image.

Thus, it can be eliminated for the observer to reversely recognize concavity and convexity when he grasps the positional relation between display regions in his observation of the three-dimensional image of a transmission image, and an errorless observation environment can be realized.

While in the foregoing embodiment, description has been made with the three-dimensional image pickup and display apparatus taken as an example, it is also possible to construct a three-dimensional image pickup and display system comprising a transmission image photographing device 201, a three-dimensional image processing device 202, a three-dimensional display 206, etc. individually combined together.

This application claims priority from Japanese Patent Application No. 2005-024807 filed Feb. 1, 2005, which is hereby incorporated by reference herein.

What is claimed is:

1. A photographing apparatus comprising:
    a plurality of radiation sources for applying a transmissive radiation ray to an object;
    a photographing unit for photographing a transmission image of the object; and
    a control unit for setting three-dimensional display parameters for observing a stereoscopically viewable image which conforms to a three-dimensional display output device;
    wherein the control unit selects the radiation source for irradiating said object in conformity with the three-dimensional display parameters and changes the position of the radiation source in conformity with the three-dimensional display parameters.

2. A photographing apparatus according to claim 1, wherein the three-dimensional display parameter comprises at lease one of the following parameters: number of view points which is number of view points the three-dimensional display output device has; display size of the three-dimensional display output device; supposed observation distance which is an observation distance supposed when an output of the three-dimensional display output device is observed; and number of steps which represents a relation between parallax images incident on right and left observing eyes when the output of the three-dimensional display output device is observed.

3. A three-dimensional image generating apparatus comprising:
    a photographing unit for photographing a transmission image of an object to which a transmissive radiation ray is applied by a radiation source;
    a control unit for setting three-dimensional display parameters for observing a stereoscopically viewable image which conforms to a three-dimensional display output device; and an image processing unit for generating an image different from the transmission image photographed by the photographing unit, on the basis of the three-dimensional display parameters, wherein the radiation source is one of a plurality of radiation sources, and wherein the control unit selects the radiation source for irradiating said object in conformity with said three-dimensional display parameters.

4. A three-dimensional image generating apparatus according to claim 3, wherein said image processing unit generates an image corresponding to a view point position different from said transmission image.

5. A three-dimensional image generating apparatus according to claim 3, wherein said image processing unit generates an image on the basis of a pixel data of said transmission image.

6. A three-dimensional image generating apparatus according to claim 3, wherein said image processing unit mirroring processes said transmission image to thereby generate an image.

7. A three-dimensional image generating apparatus according to claim 3, wherein said control unit changes the position of said radiation source on the basis of said three-dimensional display parameters.

8. A three-dimensional image generating apparatus according to claim 3, wherein the three-dimensional display parameter comprises at lease one of the following parameters: number of view points which is number of view points the three-dimensional display output device has; display size of the three-dimensional display output device; supposed observation distance which is an observation distance supposed when an output of the three-dimensional display output device is observed; and number of steps which represents a relation between parallax images incident on right and left observing eyes when the output of the three-dimensional display output device is observed.

9. A three-dimensional image generating apparatus comprising:

a photographing unit for photographing a transmission image of an object to which a transmissive radiation ray is applied by a radiation source;

a control unit for setting three-dimensional display parameters for observing a stereoscopically viewable image which conforms to a three-dimensional display output device; and an image processing unit for generating an image different from the transmission image photographed by the photographing unit, on the basis of the three-dimensional display parameters, wherein the image processing unit mirroring processes said transmission image to thereby generate an image, and wherein the control unit changes the position of the radiation source in conformity with the three-dimensional display parameters.

10. A three-dimensional image generating apparatus according to claim 9, wherein the three-dimensional display parameter comprises at lease one of the following parameters: number of view points which is number of view points the three-dimensional display output device has; display size of the three-dimensional display output device; supposed observation distance which is an observation distance supposed when an output of the three-dimensional display output device is observed; and number of steps which represents a relation between parallax images incident on right and left observing eyes when the output of the three-dimensional display output device is observed.

* * * * *